US010710076B2

(12) United States Patent
Oliphant et al.

(10) Patent No.: US 10,710,076 B2
(45) Date of Patent: Jul. 14, 2020

(54) MIXED-PHASE FLUIDS FOR NUCLEIC ACID SEQUENCING AND OTHER ANALYTICAL ASSAYS

(71) Applicant: OMNIOME, INC., San Diego, CA (US)

(72) Inventors: Arnold Oliphant, Morgan Hill, CA (US); Alex Nemiroski, San Diego, CA (US); Julian Sean Alberni, Le Mesa, CA (US); Michael John Erickstad, San Diego, CA (US); Rebecca McGinley, San Diego, CA (US); Chad Fleischer, San Diego, CA (US); Eric Villarreal, Cardiff by the Sea, CA (US)

(73) Assignee: OMNIOME, INC., San Diego, CA (US)

( * ) Notice: Subject to any disclaimer, the term of this patent is extended or adjusted under 35 U.S.C. 154(b) by 0 days.

(21) Appl. No.: 16/700,422

(22) Filed: Dec. 2, 2019

(65) Prior Publication Data
US 2020/0171498 A1 Jun. 4, 2020

Related U.S. Application Data

(60) Provisional application No. 62/930,688, filed on Nov. 5, 2019, provisional application No. 62/883,276, filed on Aug. 6, 2019, provisional application No. 62/774,998, filed on Dec. 4, 2018.

(51) Int. Cl.
*B01L 3/00* (2006.01)
*C12Q 1/6825* (2018.01)
*C12Q 1/6874* (2018.01)

(52) U.S. Cl.
CPC ... *B01L 3/502776* (2013.01); *B01L 3/502746* (2013.01); *C12Q 1/6825* (2013.01); *C12Q 1/6874* (2013.01); *B01L 2200/16* (2013.01); *B01L 2300/0816* (2013.01); *B01L 2300/0819* (2013.01); *B01L 2300/0883* (2013.01); *B01L 2400/0403* (2013.01)

(58) Field of Classification Search
CPC .................... C12Q 1/6825; B01L 3/502746
See application file for complete search history.

(56) References Cited

U.S. PATENT DOCUMENTS

| | | |
|---|---|---|
| 5,130,238 A | 7/1992 | Malek et al. |
| 5,455,166 A | 10/1995 | Walker |
| 5,641,658 A | 6/1997 | Adams et al. |
| 5,695,934 A | 12/1997 | Brenner |
| 5,863,722 A | 1/1999 | Brenner |
| 5,888,737 A | 3/1999 | DuBridge et al. |
| 6,140,489 A | 10/2000 | Brenner |
| 6,175,002 B1 | 1/2001 | Dubridge et al. |
| 6,214,587 B1 | 4/2001 | Dattagupta et al. |
| 6,266,459 B1 | 7/2001 | Walt et al. |
| 6,326,211 B1 | 12/2001 | Anderson et al. |
| 6,355,431 B1 | 3/2002 | Chee et al. |
| 6,485,918 B1 | 11/2002 | Schermer et al. |
| 6,770,441 B2 | 8/2004 | Dickinson et al. |
| 6,859,570 B2 | 2/2005 | Walt et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,337,782 B2 | 3/2008 | Thompson |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,482,120 B2 | 1/2009 | Buzby |
| 7,544,794 B1 | 6/2009 | Benner |
| 7,622,294 B2 | 11/2009 | Walt et al. |
| 7,956,171 B2 | 6/2011 | Siddiqi et al. |
| 8,034,923 B1 | 10/2011 | Benner et al. |
| 8,071,755 B2 | 12/2011 | Efcavitch et al. |
| 8,252,911 B2 | 8/2012 | Bjornson et al. |
| 8,530,164 B2 | 9/2013 | Patel et al. |
| 8,613,325 B2 | 12/2013 | Guse |

(Continued)

FOREIGN PATENT DOCUMENTS

| | | |
|---|---|---|
| WO | 9106678 | 5/1991 |
| WO | 0063437 | 6/2002 |

(Continued)

OTHER PUBLICATIONS

Clarkson et al., "Protein denaturation in foam: I. Mechanism study", J Colloid Interface Sci. 215(2), 1999, 323-332.

Dressman et al., "Transforming Single DNA Molecules into Fluorescent Magnetic Particles for Detection and Enumeration of Genetic Variations", Proceedings of the National Academy of Sciences of the United States of America, vol. 100, No. 15, Jul. 22, 2003, pp. 8817-8822.

(Continued)

*Primary Examiner* — Narayan K Bhat

(74) *Attorney, Agent, or Firm* — Kilpatrick Townsend & Stockton LLP

(57) ABSTRACT

An analytical system that includes a flow cell, a liquid delivery component, a gas delivery component and a bubble generator component, wherein the liquid delivery component is configured to deliver liquid from one or more reservoirs to the bubble generator component, wherein the gas delivery component is configured to deliver gas from one or more source to the bubble generator component, and wherein the bubble generator component is configured to mix liquids from the liquid delivery component with gas from the gas delivery component to deliver a fluid foam to the inside of the flow cell, wherein the fluid foam includes bubbles of the gas in the liquid.

24 Claims, 16 Drawing Sheets

(56) References Cited

U.S. PATENT DOCUMENTS

| | | |
|---|---|---|
| 8,808,989 B1 | 8/2014 | Efcavitch et al. |
| 8,951,781 B2 | 2/2015 | Williamson et al. |
| 9,146,248 B2 | 9/2015 | Hagerott et al. |
| 9,164,053 B2 | 10/2015 | Collins et al. |
| 9,193,996 B2 | 11/2015 | Buermann et al. |
| 9,399,798 B2 | 7/2016 | Stupi et al. |
| 9,629,939 B2 | 4/2017 | Flynn et al. |
| 9,650,669 B2 | 5/2017 | Buermann et al. |
| 9,829,456 B1 | 11/2017 | Jin et al. |
| 9,943,847 B2 | 4/2018 | Gilbert et al. |
| 9,951,385 B1 | 4/2018 | Vijayan et al. |
| 10,036,064 B2 | 7/2018 | Merriman et al. |
| 10,125,391 B2 | 11/2018 | Turner et al. |
| 10,156,509 B2 | 12/2018 | Andersen et al. |
| 10,208,332 B2 | 2/2019 | Eberhart et al. |
| 10,227,636 B2 | 3/2019 | Segale et al. |
| 10,388,498 B2 | 8/2019 | Schuethe |
| 10,400,272 B1 | 9/2019 | Middleton et al. |
| 10,443,098 B2 | 10/2019 | Vijayan et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2004/0125424 A1 | 7/2004 | Moon et al. |
| 2004/0132205 A1 | 7/2004 | Moon et al. |
| 2004/0233485 A1 | 11/2004 | Moon et al. |
| 2004/0263923 A1 | 12/2004 | Moon et al. |
| 2005/0064460 A1 | 3/2005 | Holliger et al. |
| 2005/0130173 A1 | 6/2005 | Leamon et al. |
| 2007/0007991 A1 | 1/2007 | Lee et al. |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2009/0247414 A1 | 10/2009 | Obradovic et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2010/0323350 A1* | 12/2010 | Gordon ............. B01L 3/502761 435/6.16 |
| 2012/0270305 A1 | 10/2012 | Reed et al. |
| 2014/0259607 A1* | 9/2014 | Hagerott ................ G01N 35/10 29/428 |
| 2016/0001249 A1 | 1/2016 | Light et al. |
| 2017/0022553 A1 | 1/2017 | Vijayan et al. |
| 2017/0240962 A1 | 8/2017 | Merriman et al. |
| 2017/0314072 A1 | 11/2017 | Vijayan et al. |
| 2018/0051316 A1 | 2/2018 | Collins et al. |
| 2018/0112265 A1 | 4/2018 | Boyanov et al. |
| 2018/0155698 A1 | 6/2018 | Iyidogan et al. |
| 2018/0155773 A1 | 6/2018 | Gunderson et al. |
| 2018/0305727 A1 | 10/2018 | Merriman et al. |
| 2018/0305749 A1 | 10/2018 | Stromberg et al. |
| 2019/0055598 A1 | 2/2019 | Buermann et al. |

FOREIGN PATENT DOCUMENTS

| | | |
|---|---|---|
| WO | 2004018497 | 3/2004 |
| WO | 2005010145 | 2/2005 |
| WO | 2005065814 | 7/2005 |
| WO | 2007123744 | 11/2007 |
| WO | 2012145574 A2 | 10/2012 |
| WO | 2014159409 A1 | 10/2014 |
| WO | 2015153816 A2 | 10/2015 |
| WO | 2016064755 A2 | 4/2016 |

OTHER PUBLICATIONS

Garstecki et al., "Formation of bubbles and droplets in microfluidic systems", Bulletin of the Polish Academy of Sciences: Technical Sciences, 2005.

GB1917555.3, "Official Action", dated Jan. 30, 2020, 7 pages.

PCT/US2019/063962, "International Search Report and Written Opinion", dated Feb. 28, 2020, 11 pages.

* cited by examiner

A (no foam)

B (+ foam)

MIXED-PHASE FLUIDS FOR NUCLEIC ACID SEQUENCING AND OTHER ANALYTICAL ASSAYS

This application is based on, and claims the benefit of, U.S. Provisional Application No. 62/930,688, filed Nov. 5, 2019, U.S. Provisional Application No. 62/883,276, filed Aug. 6, 2019, and U.S. Provisional Application No. 62/774,998, filed Dec. 4, 2018, each of which is incorporated herein by reference.

BACKGROUND

The present disclosure relates generally to molecular assays and has specific applicability to nucleic acid sequencing procedures.

Accurate sequence determination of a template nucleic acid strand is important for molecular diagnostics. Identification of a single nucleotide base from among alternatives at a known position can serve as the basis for analysis of single nucleotide polymorphisms (i.e., "SNPs"). A SNP can in turn be used to determine a phenotype for the individual such as susceptibility to a disease or propensity for having a desirable trait. Detecting genetic variants in a patient can indicate the efficacy for certain medications to treat the patient or the risk of adverse side effects when treating the patient with certain medications.

Commercially available nucleic acid sequencing platforms have vastly increased our knowledge of the genetic underpinnings of actionable traits. Improvements in sequencing biochemistry and detection hardware continue. However, the cost of currently available sequencing platforms has inhibited uptake of sequencing in the clinic despite broad use in research laboratories. Also, sequencing platforms are relatively slow in terms of providing a diagnostic or prognostic answer on a timeframe that matches expectations of patients and the doctors that treat them. The present disclosure provides fluidics systems and methods that reduce sequencing time, lower costs of sequencing, reduce reagent volume and provide related advantages as well.

The systems and methods of the present disclosure can be used for chemical and biological assays beyond nucleic acid sequencing.

BRIEF SUMMARY

The present disclosure provides a system for evaluating biological or chemical analytes (e.g. for sequencing nucleic acids). The system can include a stage, a liquid delivery component, a delivery component for a second phase and a phase mixing component, wherein the liquid forms a first phase that is immiscible with the second phase, wherein the stage is configured to accept a flow cell, wherein the liquid delivery component is configured to deliver liquid from one or more reservoirs to the phase mixing component, wherein the delivery component for the second phase is configured to provide the second phase to the phase mixing component, and wherein the phase mixing component is configured to mix liquids from the liquid delivery component with the second phase to deliver a mixed-phase fluid to the inside of the flow cell, wherein the mixed-phase fluid includes bubbles, globules or particles of the second phase in the liquid.

In some configurations, a system of the present disclosure can include a stage, a liquid delivery component, a gas delivery component and a bubble generator component, wherein the stage is configured to accept a flow cell, wherein the liquid delivery component is configured to deliver liquid from one or more reservoirs to the inside of the flow cell, wherein the gas delivery component is configured to deliver gas from one or more source to the bubble generator component, and wherein the bubble generator component is configured to introduce bubbles from the gas delivery component into the liquid from the liquid delivery component to deliver a fluid foam to the inside of the flow cell, wherein the fluid foam includes bubbles of the gas in the liquid.

In some configurations, a system of the present disclosure can include a stage, a first liquid delivery component, a second liquid delivery component and a phase mixing component, wherein the first liquid is immiscible with the second liquid, wherein the stage is configured to accept a flow cell, wherein the first liquid delivery component is configured to deliver the first liquid from one or more reservoirs to the phase mixing component, wherein the second liquid delivery component is configured to deliver the second liquid from one or more source to the phase mixing component, and wherein the phase mixing component is configured to mix the first and second liquid to deliver an emulsion to the inside of the flow cell, wherein the emulsion includes globules of the second liquid in the first liquid.

In some configurations, a system of the present disclosure can include a stage, a liquid delivery component, a particle delivery component and a phase mixing component, wherein the particle is immiscible with the liquid, wherein the stage is configured to accept a flow cell, wherein the liquid delivery component is configured to deliver liquid from one or more reservoirs to the phase mixing component, wherein the particle delivery component is configured to provide the particles to the phase mixing component, and wherein the phase mixing component is configured to mix liquids from the liquid delivery component with the particles to deliver a fluid slurry to the inside of the flow cell, wherein the fluid slurry includes particles in the liquid.

Also provided is a method for detecting a molecular analyte (e.g. a protein or nucleic acid), the method including steps of (a) providing a detection system including a flow cell having the molecular analyte therein; (b) delivering a series of fluids to the inside of the flow cell to modify the molecular analyte, wherein at least one of the fluids is a mixed-phase fluid that includes bubbles, globules or particles of the second phase suspended in the liquid phase; and (c) detecting the molecular analyte that is modified in step (b).

A method for sequencing a nucleic acid can include steps of (a) providing a sequencing system including (i) a flow cell having a nucleic acid immobilized therein, (ii) a phase mixing component that mixes a liquid phase with a second phase at a predefined rate; (b) delivering a series of fluids to the inside of the flow cell to perform a cycle of a sequencing process, wherein at least one of the fluids is a mixed-phase fluid produced by the phase mixing component to include bubbles, globules or particles of the second phase suspended in the liquid phase; and (c) repeating step (b), thereby determining the sequence for the nucleic acid.

A method for sequencing a nucleic acid can include steps of (a) providing a sequencing system including (i) a flow cell having a nucleic acid immobilized therein, (ii) a bubble generator component that delivers gas to a liquid at a predefined rate; (b) delivering a series of fluids to the inside of the flow cell to perform a cycle of a sequencing process, wherein at least one of the fluids is a fluid foam produced by the bubble generator component to include bubbles of the gas in a liquid; and (c) repeating step (b), thereby determining the sequence for the nucleic acid.

A method for sequencing a nucleic acid can include steps of (a) providing a sequencing system including (i) a flow cell having a nucleic acid immobilized therein, (ii) a phase mixing component that mixes a first liquid with a second liquid at a predefined rate; (b) delivering a series of fluids to the inside of the flow cell to perform a cycle of a sequencing process, wherein at least one of the fluids is an emulsion produced by the phase mixing component to include globules of the second liquid in the first liquid; and (c) repeating step (b), thereby determining the sequence for the nucleic acid.

A method for sequencing a nucleic acid can include steps of (a) providing a sequencing system including (i) a flow cell having a nucleic acid immobilized therein, (ii) a phase mixing component that mixes a liquid with solid-phase particles at a predefined rate; (b) delivering a series of fluids to the inside of the flow cell to perform a cycle of a sequencing process, wherein at least one of the fluids is a fluid slurry produced by the phase mixing component to include the particles in the liquid; and (c) repeating step (b), thereby determining the sequence for the nucleic acid.

Further provided is a flow cell that includes a stabilized ternary complex immobilized inside the flow cell, wherein the stabilized ternary complex includes a polymerase, a primed template nucleic acid and a next correct nucleotide for the template; and a mixed-phase fluid including a plurality of gas bubbles, liquid globules or particles in a liquid, wherein the mixed-phase fluid is in contact with the stabilized ternary complex.

In another aspect, a flow cell can include a luminescently labelled nucleic acid that is immobilized inside a flow cell, and a mixed-phase fluid including a plurality of gas bubbles, liquid globules or particles in a liquid, wherein the mixed-phase fluid is in contact with the luminescently labelled nucleic acid.

In a further aspect, a flow cell can include a reversibly terminated nucleic acid that is immobilized inside a flow cell, and a mixed-phase fluid including a plurality of gas bubbles, liquid globules or particles in a liquid, wherein the mixed-phase fluid is in contact with the reversibly terminated nucleic acid.

DETAILED DESCRIPTION

Figure 1:
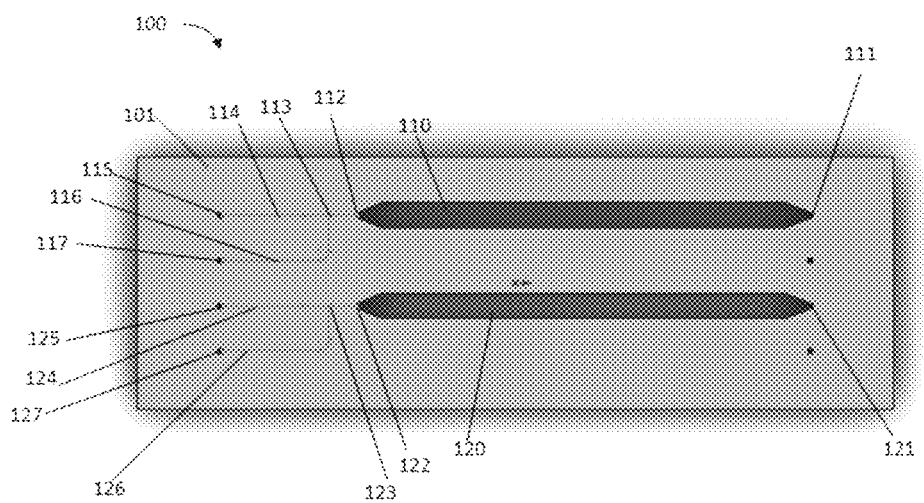
FIG. 1 shows a flow cell having two detection channels, each of the detection channels being fluidically connected to a gas mixing component, the gas mixing component using a T junction to connect a liquid channel and a gas channel.

Bubbles have been known to have adverse impacts on molecular analyses such as nucleic acid sequencing processes and protein activity assays. Accordingly, avoidance or removal of bubbles has previously been a design goal and user requirement for methods and apparatus that are used in molecular analyses. Analytical methods that are typically configured to avoid bubbles include, for example, those in which a protein is contacted with analytes of interest under conditions where the proteins bind to the analytes or where the proteins catalyze a change to the analytes. The binding or catalysis can produce a signal or other detectable event that is indicative of the presence, quantity, composition, function or other characteristic of the protein and/or analyte. The analytical methods are typically carried out in liquids that are formulated to maintain stability of the reaction components especially the proteins. Bubbles are believed to damage proteins due to surface denaturation at the gas-liquid interface. See, for example, Clarkson et al., *J Colloid Interface Sci.* 215(2):323-332 (1999), which is incorporated herein by reference. As a result, bubbles are avoided in molecular analyses, especially those that utilize proteins.

Bubbles can also cause interference for the detection devices that are used for many molecular analyses such as nucleic acid sequencing processes and protein activity assays. For example, a bubble that passes into the optical path of a luminescence detector will scatter the light that would otherwise be detected. Many sequencing processes and other analytical assays utilize solid phase substrates. In these assays liquid reagents interact with analytes on a surface to produce a detectable product or signal. However, bubbles that adhere to the surface can scatter optical signals and can block the liquid reagents from contacting the analytes, at least temporarily, and may permanently damage the analytes by drying them out.

Bubbles are routinely avoided in molecular analyses such as nucleic acid sequencing processes and protein activity assays due to a perception that problems will arise, such as those set forth above. The present disclosure provides systems and methods that employ bubbles to good use in nucleic acid sequencing processes and other analytical methods. Surprisingly it has been found that bubbles can be introduced into a liquid stream to produce a fluid foam that is, in turn, capable of participating in one or more steps of a nucleic acid sequencing reaction. The bubbles can be introduced into the liquid stream under controlled conditions to have a variety of desired effects and to avoid unwanted outcomes. For example, a fluid foam can be used to wash a solid support upon which a sequencing reaction takes place, for example, providing relatively efficient removal of a previously delivered solution and replacement with a new solution. Packing density of the bubbles in the fluid foam can be adjusted to influence the efficiency of fluid exchange. Efficient exchange can be facilitated by using a fluid foam having densely packed bubbles. A collection of densely packed bubbles is difficult to penetrate diffusively because the bubbles provide physical obstacles to diffusion. Therefore, dense packing of bubbles can allow better segregation between the reagents of two fluids that are introduced to a flow cell in series.

Furthermore, the flow of a fluid foam through a channel has a different profile than a liquid laminar flow. A laminar flow has a parabolic velocity profile (faster in the center, slower on the outside). In a flow of fluid foam the bubbles can be maintained in lock-step, for example, by appropriate choice of flow rate, and flow together. This helps with exchange of one fluid for another because the foam preserves a flat front regardless of how far it has propagated through the system. Reduced diffusion between proximal flowing fluids, as well as reduced velocity shearing can help preserve each fluid reagent slug as it propagates through a flow cell or other fluidic channel, and together, these two effects can reduce the amount of time required to achieve a particular level of fluid exchange compared to the time that would be required for a non-foam fluid to achieve the same level of exchange for the same fluid reagents.

Moreover, bubbles can facilitate mixing within a solution to increase efficiency of reagent transfer between a fluid foam and the surface of a solid support. Rapid convective diffusion near bubbles can increase the reaction rate of diffusion limited kinetics near the surface by replenishing (or completely disrupting) the depletion region. A further advantage of using bubbles is a reduction in reagent cost due to a reduction in the volume or amount of fluid utilized. More specifically, because gases used to produce bubbles are cheaper than many reagents used for nucleic acid sequencing, and because a relatively high volume of fluid can be required to perform particular step(s) of a sequencing reaction, adding bubbles to the fluid can act as an inert filler to reduce the amount of reagent fluid consumed to effectively perform the particular step(s). Controlled delivery and removal of bubbles as set forth herein can allow bubbles to be cleared from a flow cell when desired, for example, to facilitate optical detection of the flow cell interior. Other inert fillers in a bulk liquid, such as particles or liquids that are immiscible with the bulk liquid, can provide advantages similar to those set forth above for bubbles.

Bubbles can be used for improved thermoregulation, for example, when pre-equilibrating solutions to the temperature of a flow cell or other fluidic channel. For example, the temperature of a liquid reagent can be increased or decreased by introducing a gas that is heated or chilled, respectively. The bubbles in the resulting foam provide a high surface area of contact with the bulk liquid phase and this can facilitate rapid and efficient change in the temperature of the reagents in the bulk liquid. Dispersed phase materials other than bubbles, such as particles or immiscible liquids, can provide similar advantages for controlling temperature when added to a bulk phase liquid to form a mixed-phase fluid.

A fluid foam can also be used to remove other bubbles, for example, surface bubbles that are otherwise difficult to dislodge from a surface. Foams are capable of dislodging surface bubbles in some situations more efficiently than homogenous liquids that are composed similarly to the bulk phase of the foams. Bubbles can also provide a useful visual aid for determining flow rates in a flow cell.

The present disclosure sets forth systems, apparatus and methods that employ fluid foam. The fluid foam can be replaced with other mixed-phase fluids such as fluid emulsions or fluid particle slurries to achieve similar results. Accordingly, many configurations of the apparatus and methods set forth below need not be limited to the use of fluid foam and can employ other mixed-phase fluids instead.

Terms used herein will be understood to take on their ordinary meaning in the relevant art unless specified otherwise. Several terms used herein and their meanings are set forth below.

As used herein, the term "array" refers to a population of molecules that are attached to one or more solid supports such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates, primed nucleic acid templates or nucleic acid enzymes such as polymerases, ligases, exonucleases or combinations thereof.

As used herein, the term "attached" refers to the state of two things being joined, fastened, adhered, connected or bound to each other. For example, a reaction component, such as a primed template nucleic acid or a polymerase, can be attached to a solid phase component by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "binary complex," when used in reference to a polymerase, refers to an intermolecular association between the polymerase and a nucleic acid such as a primed template nucleic acid, but excluding monomeric nucleotide molecules such as a next correct nucleotide of the primed template nucleic acid.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversible terminator" nucleotide can be removed from the nucleotide analog, or otherwise modified, to allow the 3'-oxygen of the nucleotide to covalently link to a next correct nucleotide. This process is referred to as "deblocking" the nucleotide analog. Such a blocking moiety is referred to herein as a "reversible terminator moiety." Exemplary reversible terminator moieties are set forth in U.S. Pat. No. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid.

As used herein, the term "bubble" refers to a globule of gas within a liquid or solid. A bubble can be observed in a fluid due to the gas having a different refractive index compared to the surrounding liquid. A bubble that is completely surrounded by liquid is referred to as a "bulk bubble." A bubble that is attached to a solid phase surface is referred to as a "surface bubble."

As used herein, the term "catalytic metal ion" refers to a metal ion that facilitates phosphodiester bond formation between the 3'-oxygen of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-oxygen of a nucleic acid (e.g., a primer) and the phosphate moiety of an incoming nucleotide. Exemplary catalytic metal ions include $Mg^{2+}$ and $Mn^{2+}$.

The term "comprising" is intended herein to be open-ended, including not only the recited elements, but further encompassing any additional elements.

As used herein, the term "cycle," when used in reference to a sequencing process, refer to the portion of a sequencing run that is repeated to indicate the presence of a nucleotide. Typically, a cycle includes several steps such as steps for delivery of reagents, washing away unreacted reagents and detection of signals indicative of changes occurring in response to added reagents.

As used herein, the term "diffusional exchange," when used in reference to members of a binding complex, refers to the ability of the members to move in a fluid to associate with, or dissociate from, each other. Diffusional exchange can occur when there are no barriers that prevent the members from interacting with each other to form a complex. However, diffusional exchange is understood to exist even if diffusion is retarded, reduced or altered so long as access is not absolutely prevented.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, "equilibrium" refers to a state of balance due to the equal action of opposing forces. For example, a ternary complex formed between a primed template nucleic acid, polymerase, and cognate nucleotide is in equilibrium with non-bound polymerase and non-bound nucleotide when the rate of formation of the ternary complex is balanced by the rate of its dissociation. Under this condition, the reversible binding reaction ceases to change its net ratio of products (e.g. ternary complex) to reactants (e.g. polymerase, nucleotide and nucleic acid). If the rate of a forward reaction (e.g., ternary complex formation) is balanced by the rate of a reverse reaction (e.g., ternary complex dissociation), then there is no net change in the ratio of products to reactants.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, a "flow cell" is a reaction chamber that includes one or more channels that direct fluid to a detection zone. The detection zone can be functionally coupled to a detector such that a reaction occurring in the reaction chamber can be observed. For example, a flow cell can contain primed template nucleic acid molecules tethered to a surface, to which nucleotides and ancillary reagents are iteratively applied and washed away. The flow cell can include a transparent material that permits the sample to be imaged after a desired reaction occurs. For example, a flow cell can include a glass or plastic slide containing detection channels through which polymerases, dNTPs and buffers can be pumped. The glass or plastic inside the channels can be decorated with one or more primed template nucleic acid molecules to be sequenced. An external imaging system can be positioned to detect the molecules at a detection zone in the detection channel or on a surface in the detection channel. Exemplary flow cells, methods for their manufacture and methods for their use are described in US Pat. App. Publ. Nos. 2010/0111768 A1 or 2012/0270305 A1; or WO 05/065814, each of which is incorporated by reference herein.

As used herein, the term "fluid" refers to a liquid or a gas, that is capable of flowing and that changes its shape to fill a vessel. In many conditions, a fluid will change shape at a steady rate when acted upon by a force tending to change its shape.

As used herein, the term "fluid emulsion" refers to a first liquid that contains globules of a second liquid, the globules being immiscible with the first liquid. The first liquid functions as a dispersion phase (also known as a bulk phase) and the globules function as a dispersed phase. Exemplary dispersion phase liquids include those that contain reagents or products of a reaction such as a binding reaction, nucleic acid sequencing reaction or reaction used in an analytical assay. Aqueous liquids provide a particularly useful dispersion phase. Exemplary globules that can be present in aqueous liquid include, but are not limited to, oils, micelles, liposomes or vesicles. A fluid emulsion can contain one or both of bulk globules (i.e. globules surrounded by liquid) and surface globules (globules in contact with a solid-support surface such as a flow cell surface). In some configurations, a fluid emulsion can be substantially devoid of either bulk globules or surface globules. A fluid microemulsion will have globules with average diameter that is equal or smaller than 1 micron, whereas a fluid macroemulsion will have globules with average diameter larger than 1 micron.

As used herein, the term "fluid foam" refers to liquid that contains bubbles of gas. The liquid functions as a dispersion phase and the bubbles function as a dispersed phase. Exemplary dispersion phase liquids include those that contain reagents or products of a reaction such as a binding reaction, nucleic acid sequencing reaction or reaction used in an analytical assay. Aqueous liquids provide a particularly useful dispersion phase. Exemplary gases include inert gases such as nitrogen ($N_2$) or noble gases. Useful noble gases include, for example, helium (He), neon (Ne), argon (Ar), krypton (Kr) and xenon (Xe). Another useful gas is atmospheric air of planet earth. A fluid foam can contain one or both of bulk bubbles (i.e. bubbles surrounded by liquid) and surface bubbles (bubbles in contact with a solid-support surface such as a flow cell surface). In some configurations, a fluid foam can be substantially devoid of either bulk bubbles or surface bubbles. A fluid microfoam will have bubbles with average diameter that is equal or smaller than 1 micron, whereas a fluid macrofoam will have bubbles with average diameter larger than 1 micron.

As used herein, the term "fluid slurry" refers to liquid that contains solid-phase particles. The liquid functions as a dispersion phase (also known as a bulk phase) and the particles function as a dispersed phase. Exemplary dispersion phase liquids include those that contain reagents or products of a reaction such as a binding reaction, nucleic acid sequencing reaction or reaction used in an analytical assay. Aqueous liquids provide a particularly useful dispersion phase. Exemplary solid-phase materials include those set forth herein in the context of arrays and beads. A fluid slurry can contain one or both of bulk particles (i.e. particles surrounded by liquid) and surface particles (particles in contact with the surface of another solid-support such as a flow cell). In some configurations, a fluid slurry can be substantially devoid of either bulk particles or surface particles. A fluid microslurry will have particles with average diameter that is equal or smaller than 1 micron, whereas a fluid macroslurry will have particles with average diameter larger than 1 micron.

As used herein, the term "fluidically coupled," when used in reference to two things, means that a fluid, or solute in the fluid, is capable of transferring from one of the things to the other. For example, a reservoir can be fluidically coupled to a flow cell via a tube through which fluid can flow. In another example, two sites in an array are fluidically coupled if the array resides in a liquid such that a solute can diffuse from one site to the other.

As used herein, the terms "free" or "non-bound," when used in reference to components that are capable of forming a complex in a binding reaction, refers to components that are not in a bound state. By way of example, an equilibrium binding reaction can include a product (e.g. a ternary complex) and reactants that are not bound up in the product (e.g. free polymerases, free nucleic acids or free nucleotides).

As used herein, the term "globule" refers to a droplet of a first liquid within a second liquid, wherein the first liquid is immiscible with the second liquid. A globule can be observed in a fluid due to the globule having a different refractive index compared to the surrounding liquid. A globule that is completely surrounded by liquid is referred to as a "bulk globule." A globule that is attached to a solid phase surface is referred to as a "surface globule."

As used herein, the term "inhibitory metal ion" refers to a metal ion that, when in the presence of a polymerase enzyme, inhibits phosphodiester bond formation needed for chemical incorporation of a nucleotide into a primer. An inhibitory metal ion may interact with a polymerase, for example, via competitive binding compared to catalytic metal ions. A "divalent inhibitory metal ion" is an inhibitory metal ion having a valence of two. Examples of divalent inhibitory metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are inhibitory metal ions having a valence of three.

As used herein, the term "immobilized," when used in reference to a molecule, refers to direct or indirect, covalent or non-covalent attachment of the molecule to a solid support. In some configurations, covalent attachment may be preferred, but generally all that is required is that the molecules (e.g. nucleic acids) remain immobilized or attached to the support under the conditions in which it is intended to use the support, for example, in applications that utilize immobilization of nucleic acid or polymerase at or near a sensor.

As used herein, the term "label" refers to a molecule or moiety thereof that provides a detectable characteristic. The detectable characteristic can be, for example, an optical signal such as absorbance of radiation, luminescence or fluorescence emission, luminescence or fluorescence lifetime, luminescence or fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, or the like.

As used herein, the term "ligand" refers to a molecule that binds to another molecule (or complex of molecules), such as a receptor. Example ligands include peptides or polypeptides, antibodies, hormones, small molecule drugs, nucleic acids, nucleotides, etc. Ligands can be naturally occurring or synthetic molecules. The combination of a ligand bound to a receptor by a reversible association can be termed a "receptor-ligand complex."

As used herein, the term "mixed-phase," when used in reference to a fluid, means, a liquid that contains a suspension of gas bubbles, liquid globules or solid particles that are not miscible with the liquid. Exemplary mixed-phase fluids include, but are not limited to, a fluid foam (gas bubbles in liquid), fluid emulsion (globules of a first liquid that are immiscible with a surrounding second liquid), fluid slurry (solid particles in liquid). Exemplary liquids include those that contain reagents or products of a reaction such as a binding reaction, nucleic acid sequencing reaction, synthetic reaction or reaction used in an analytical assay.

As used herein, the term "next correct nucleotide" refers to the nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact specifically with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), exogenously labelled nucleotides, or non-natural analogs thereof such as dideoxyribonucleotide triphosphates (ddNTPs) or reversibly terminated nucleotide triphosphates (rtNTPs).

As used herein, the term "particle," when used in reference to a fluid slurry, refers to a solid phase material within a liquid phase, wherein the solid is not dissolved in the liquid. A particle can be observed in a fluid due to the particle having a different refractive index or optical transmittance compared to the surrounding liquid. A particle that is completely surrounded by liquid is referred to as a "bulk particle." A particle that is attached to a solid phase surface is referred to as a "surface particle."

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation. The amount of polymerase in a fluid can be quantified in activity units. For example, a unit of polymerase can be equal to the amount of enzyme catalyzing the incorporation of 10 nmol of dNTP into DNA in 30 min at a particular temperature. For example, thermostable polymerases can be measured at 75° C., whereas thermolabile polymerases can be measured at 37° C.

As used herein, the term "predefined," when used in reference to a functional characteristic of a system, means that the characteristic is a known, predictable or expected result of a manipulation to the system that is intended to produce the characteristic. For example, foaminess of a fluid is a known and expected result of introducing bubbles into a liquid using a bubble generator such as a gas-liquid mixing system. Exemplary predefined characteristics of a system can optionally include the rate at which a dispersed phase is formed in a bulk phase, the amount of dispersed phase that is introduced into a bulk phase, the relative ratio of dispersed phase and bulk phase that is produced by the system, the size of dispersed phase elements (e.g. bubbles, particles or globules) that is produced by the system, or the like.

As used herein, the term "primed template nucleic acid" refers to a nucleic acid hybrid having a double stranded region such that one of the strands has a 3'-end that can be extended by a polymerase. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid sequence at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence (e.g. a dissociable primer). A primer can consist of DNA, RNA or analogs thereof. A primer can be blocked at the 3' end or it can be extendable.

As used herein, the term "receptor" refers to a chemical group or molecule (such as a protein) that has an affinity for another specific chemical group or molecule. Example receptors include proteins on or isolated from the surface or interior of a cell, antibodies or functional fragments thereof, lectins or functional fragments thereof, avidin, streptavidin, nucleic acids that are either single- or double-stranded, etc. A primed template nucleic acid molecule bound by a polymerase can serve as a receptor for a cognate nucleotide ligand.

As used herein, the term "site," when used in reference to an array, means a location in an array where a particular molecule is present. A site can contain only a single molecule, or it can contain a population of several molecules of the same species (i.e. an ensemble of the molecules). Alternatively, a site can include a population of molecules that are different species (e.g. a population of ternary complexes having different template sequences). Sites of an array are typically discrete. The discrete sites can be contiguous, or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by at least 0.5 micron, 1 micron, 5 microns, 10 microns, 50 microns or 100 microns. The sites can each have an area of less than 1 square millimeter, 500 square microns, 100 square microns, 25 square microns, 1 square micron or less. The term "feature," when used in reference to an array is intended to be synonymous with the term "site."

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, and polymers.

As used herein, the term "substantially devoid" means being without an effective or detectable amount of a particular thing or characteristic. For example, a fluid having no bubbles, bubbles that are too small or too few to be observed by a particular system, bubbles that are too small or too few to be observed in a particular method, or bubbles that are too small or too few to have a significant effect on a reaction (e.g. on a binding reaction or sequencing reaction) can be characterized as a fluid that is substantially devoid of bubbles. By way of another example, a gas having no molecular oxygen (e.g. dioxygen ($O_2$), trioxygen or ozone ($O_3$), or singlet oxygen), a concentration of molecular oxygen that is undetectable in a system or method set forth herein, or a concentration of molecular oxygen that does not have a significant effect on a reaction (e.g. on a binding reaction or sequencing reaction) can be characterized as a gas that is substantially devoid of molecular oxygen.

As used herein, the term "surface" refers to a portion of a solid support that contacts a fluid. The fluid can be gas or liquid. The surface can be substantially flat or planar. Alternatively, the surface can be rounded or contoured. Exemplary contours that can be included on a surface are wells, depressions, pillars, ridges, channels or the like. Exemplary materials that can be used as a solid support include, but are not limited to, glass such as modified or functionalized glass; plastic such as acrylic, polystyrene or a copolymer of styrene and another material, polypropylene, polyethylene, polybutylene, polyurethane or Teflon™; nylon; nitrocellulose; resin; silica or silica-based materials including silicon and modified silicon; carbon-fiber; metal; inorganic glass; optical fiber bundle, or the like.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "type" or "species" is used to identify molecules that share the same chemical structure. For example, a mixture of nucleotides can include several dCTP molecules. The dCTP molecules will be understood to be the same type (or species) of nucleotide as each other, but a different type (or species) of nucleotide compared to dATP, dGTP, dTTP etc. Similarly, individual DNA molecules that have the same sequence of nucleotides are the same type (or species) of DNA, whereas DNA molecules with different sequences are different types (or species) of DNA. The term "type" or "species" can also identify moieties that share the same chemical structure. For example, the cytosine bases in a template nucleic acid will be understood to have the same type (or species) of base as each other independent of their position in the template sequence.

The embodiments set forth below and recited in the claims can be understood in view of the above definitions.

The present disclosure provides a sequencing system that includes a stage, a delivery component for a liquid phase, a delivery component for a second phase and a phase mixing component, wherein the liquid phase is immiscible with the second phase, wherein the stage is configured to accept a flow cell, wherein the liquid delivery component is configured to deliver liquid from one or more reservoirs to the phase mixing component, wherein the delivery component for the second phase is configured to provide the second phase to the phase mixing component, and wherein the phase mixing component is configured to mix liquids from the liquid delivery component with the second phase to deliver a mixed-phase fluid to the inside of the flow cell, wherein the mixed-phase fluid includes bubbles, globules or particles of the second phase in the liquid.

Analytical systems of the present disclosure are tangible things, having tangible components or subsystems. It will be understood that an analytical system can include a combination of tangible and intangible components or subsystems. Alternatively, an analytical system can, in some configurations, be devoid of intangible components and subsystems.

A system can be configured as a monolithic apparatus, for example, containing all of the subsystems or components utilized for a particular purpose within a single housing. Alternatively, one or more of the subsystems or components described herein can be located remotely from other components or conveniently separable from other components. For example, a nucleic acid sequencing system can include a fluidic component and detection component that are maintained together in a single housing, whereas a computer processing unit that is operably connected to the fluidic and detection components can physically reside in a separate housing. Components that are separated or remote from each other can nonetheless be functionally networked via hardware (e.g. fluidic lines, optical fibers or electrical lines) or wireless communication.

A system of the present disclosure can be configured to use a flow cell. The flow cell is an apparatus that can include a detection channel where an analytical reaction of interest can be observed. The analytical reaction can occur in bulk solution within the flow cell. For example, two solutions can be mixed and the product of the mixture can be observed in the detection channel. Alternatively, an analytical reaction can occur on a solid support within the detection channel. For example, a reagent solution can be flowed over a solid support that is attached to analytes of interest, such as nucleic acids, and a resulting reaction can be observed on the solid support. A flow cell allows convenient fluidic manipulation by passing solutions through an ingress opening, into the detection channel and out of the interior via an egress opening. The detection channel also has an observation area or volume such as an optically transparent window through which optical signals can be observed, an electrical contact through which electronic signals can be observed or the like. A particularly useful flow cell has a window that is transparent to excitation radiation and emission radiation used for luminescence detection. Exemplary flow cells that can be used for a system or method set forth herein are described, for example, in US Pat. App. Pub. No. 2010/0111768 A1, WO 05/065814 or US Pat. App. Pub. No. 2012/0270305 A1, each of which is incorporated herein by reference.

In some configurations, a reaction can occur in a first chamber, a product of the reaction can flow to a second chamber and the product can be detected in the second chamber. The reaction can occur in the presence of a mixed-phase fluid and/or the product of the reaction can be transported from the first chamber to the second chamber via flow of a mixed-phase fluid. The same or different mixed-phase fluid can be used for the reaction and the transport of the reaction product. In this example, the first and/or second chamber can be a flow cell. In some configurations, the first and second chambers can be in the same flow cell. Detection can occur in the presence of a mixed-phase fluid, in the absence of a mixed-phase fluid, prior to delivery of a mixed-phase fluid or after removal of a mixed-phase fluid.

A flow cell or similar apparatus can have one or more detection channel. The detection channel(s) can be closed to atmosphere (or other surrounding environment such as the local environment immediately surrounding the flow cell), for example, forming a tube or tunnel inside of the flow cell structure. The detection channel can have any of a variety of cross-sectional shapes including, for example, circular, oval, triangular, square, rectangular, polyhedral or other closed shapes. The cross-sectional area of the detection channel can be uniform over its length. For example, a detection channel having a circular cross-sectional area that is uniform over the length of the channel will have a cylindrical shape, whereas a detection channel having a circular cross-sectional area that is increasing or decreasing over the length of the channel will have a conical or funnel shape. The cross-sectional area of a detection channel can be at least about 1 $\mu m^2$, 10 $\mu m^2$, 100 $\mu m^2$, 1 $mm^2$, 10 $mm^2$, or 100 $mm^2$ or larger. Alternatively or additionally, the cross-sectional area of a detection channel can be at most about 100 $mm^2$, 10 $mm^2$, 1 $mm^2$, 100 $\mu m^2$, 10 $\mu m^2$, 1 $\mu m^2$, or smaller. The volume of a detection channel in a flow cell can be at least about 1 nL, 10 nL, 100 nL, 1 µL, 10 µL, 100 µL, 1 mL, 10 ml or more. Alternatively or additionally, the volume of a detection channel in a flow cell can be at most about 10 mL, 1 mL, 100 µL, 10 µL, 1 µL, 100 nL, 10 nL, 1 nL or less.

A flow cell of the present disclosure can have one or more openings for transfer of fluids. In particular configurations, a first opening can function as an ingress for the fluids and a second opening can function as an egress for the fluids. Alternatively, a flow cell can have a single opening that functions as both an ingress and egress. The fluid can be a liquid, gas or mixed-phase fluid. The flow cell can further include a region where analytes are detected. A fluid can flow into the flow cell via the ingress, then through the region and then out the egress to exit the flow cell. By way of illustrative example, the region can be examined or detected through a window in the flow cell. For example, an optical detector can observe an interior region of the flow cell through an optically transparent window of the flow cell. The region of the flow cell can be examined or observed by techniques other than optical techniques including, for example, detection techniques set forth herein. Accordingly, the flow cell can have a transmission surface that transmits signals from the region of the flow cell to the appropriate detector apparatus. It will be understood that a flow cell need not be configured for detection of analytes. For example, the flow cell can provide a chamber for a reaction to occur and a product of the reaction can flow out of the flow cell for subsequent use or detection. Accordingly, a flow cell need not have an optically transparent window or other surface that is configured for transmitting analytical signals.

In some configurations, a flow cell is a fixed component of a fluidic system, for example, requiring specialized tools and/or specialized training to remove. Alternatively, a flow cell can be a removable component of a fluidic system. For example, a system of the present disclosure can include a stage that is configured for convenient placement and removal of the flow cell. Thus, the flow cell can be a consumable component that is dedicated for use in a first analytical test and then removed to be replaced by a second flow cell used for a second analytical test. The two flow cells can be configured similarly to each other, for example, containing similar analytes, similar samples or sub-fractions of a particular sample. Alternatively, a first flow cell can be replaced with a second flow cell that is configured differently from the first. For example, the two flow cells can contain different samples or different types of analytes.

A stage can be configured for detection of a flow cell. The stage can be positionally fixed or it can be translatable. For example, a translatable stage can be moved, relative to a detector, linearly in one or more directions defined by a Cartesian coordinate system. For example, a flow cell can be translated in one or more of a first direction (e.g. to scan a swath of a flow cell along they dimension), a second direction (e.g. to shift the flow cell along the x dimension to align a second swath of the flow cell for scanning), and a third direction (e.g. to move the flow cell along the z dimension to bring it into the focus of a detector). Examples of translation stages are set forth in U.S. Pat. No. 8,951,781 or 10,227,636, each of which is incorporated herein by reference. Examples of positionally fixed stages that can be useful are set forth in U.S. Pat. No. 9,650,669, which is incorporated herein by reference. A positionally fixed stage can be useful when scanning detection is not used or when scanning is achieved by moving the detector instead of the flow cell. A fixed stage can also be configured to provide a reference surface that contacts a flow cell to align it with respect to a detector, wherein the flow cell is moved relative to the reference surface, for example, by sliding the flow cell while it is in contact with the reference surface. Exemplary systems that are configured with a reference surface and with mechanisms for sliding a flow cell along the reference surface are set forth in US Pat. App. Pub. No. 2019/0055598 A1 or U.S. Pat. App. Ser. No. 62/807,934, each of which is incorporated herein by reference.

Any of a variety of analytes can be present in a flow cell or other vessel set forth herein. The analytes can be contacted with a mixed-phase fluid. The mixed-phase fluid can be flowing or static while in contact with the analytes. Exemplary analytes include, but are not limited to, the analytes exemplified herein or in references cited herein.

Particularly useful analytes participate in nucleic acid sequencing processes. Accordingly, a flow cell can contain one or more nucleic acids, polymerases, polymerase inhibitors, polymerase cofactors (e.g. catalytic metal ions), ternary complex stabilizing agents (e.g. inhibitory metal ions), nucleotides, nucleic acid binding proteins, nucleotide deblocking reagents, or the like. Lithium or betaine can also be present, for example, in a formulation as set forth in U.S. Pat. No. 10,400,272 (App. Ser. No. 16/355,361), which is incorporated herein by reference. Accordingly, the analytes can be reactants for, or products of, a reaction such as those set forth herein.

Other analytes that can be present in a flow cell include, for example, biological tissues, biological cells; organelles; protein-based enzymes; protein-based receptors such as antibodies, lectins or streptavidin; peptides; RNA molecules; aptamers or the like. The contents of the flow cell can optionally be in contact with a mixed-phase fluid (e.g. a fluid foam, fluid slurry or fluid emulsion). Exemplary protein-based enzymes that can be used include, but are not limited to, polymerase, transposase, ligase, recombinase, kinase, phosphatase, exonuclease, endonuclease, sulfurylase, apyrase, luciferase, green fluorescent protein (GFP), or phycobiliprotein (e.g. phycocyanin, allophycocyanin, or phycoerythrin). The contact can occur during all or part of an analytical or synthetic process, such as those exemplified herein. It will be understood that one or more of the analytes set forth in the present disclosure or known in the art of biological or chemical analysis, can avoid contact with a mixed-phase fluid in one or more steps of a method set forth herein.

In some aspects, a flow cell or other vessel is provided, the flow cell including a stabilized ternary complex immobilized inside the flow cell, wherein the stabilized ternary complex includes a polymerase, a primed template nucleic acid and a next correct nucleotide for the template; and a mixed-phase fluid including a plurality of gas bubbles, liquid globules or particles in a liquid, wherein the mixed-phase fluid is in contact with the stabilized ternary complex.

In some configurations of the methods set forth herein, such as some nucleic acid sequencing methods, a mixed-phase fluid (e.g. fluid foam, fluid slurry or fluid emulsion) is used in some steps that employ a stabilized ternary complex but not in other steps that employ a stabilized ternary complex. In an exemplary configuration, a mixed-phase fluid does not contact a stabilized ternary complex until after the stabilized ternary complex has been detected. In this configuration, the mixed-phase fluid can optionally be used to dissociate the stabilized ternary complex or otherwise remove it from the flow cell. A mixed-phase fluid may or may not be used to deliver one or more components that participate in a stabilized ternary complex to a vessel such as a flow cell. Optionally a method can be configured such that it does not include any steps that contact a stabilized ternary complex with a mixed-phase fluid.

A flow cell or other vessel that is used in a system or method of the present disclosure can include a polymerase. The polymerase can be in contact with a mixed-phase fluid (e.g. a fluid foam, fluid slurry or fluid emulsion) during delivery to the flow cell or during one or more steps of a method set forth herein. Any of a variety of polymerases can be used in a method set forth herein. Reference to a particular polymerase, such as those exemplified throughout this disclosure, will be understood to include functional variants thereof unless indicated otherwise. Particularly useful functions of a polymerase include formation of a ternary complex, extension of a primer to introduce a nucleotide (such as a reversible terminated nucleotide), or catalysis of the polymerization of a nucleic acid strand using an existing nucleic acid as a template.

Polymerases can be classified based on structural homology such as the classification of polymerases into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase; Phi29 DNA polymerase; and RB69 bacteriophage DNA polymerase. Family C includes, for example, the *E. coli* DNA Polymerase III alpha subunit. Family B archaeon DNA polymerases include, for example, Vent, Deep Vent, Pfu and 9° N (e.g., Therminator™ DNA polymerase from New England BioLabs Inc.; Ipswich, Mass.) polymerases. Family D includes, for example, polymerases derived from the Euryarchaeota subdomain of Archaea. DNA Polymerases in Family X include, for example, eukaryotic polymerases Pol β, pot σ, Pol λ, and Pol μ, and *S. cerevisiae* Pol4. DNA Polymerases in Family Y include, for example, Pol η, Pol ι, Pol κ, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

Further examples of useful DNA polymerases include bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator™ DNA polymerase from New England BioLabs Inc.; Ipswich, Mass.) can be used.

Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some applications of the methods and systems set forth herein. Polymerases that substantially lack 3'-5' proofreading exonuclease activity are also useful in some configurations, for example, in most sequencing systems and methods. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Polymerases that may be used in a method or composition set forth herein include naturally occurring polymerases and modified variations thereof, including, but not limited to, mutants, recombinants, fusions, genetic modifications, chemical modifications, synthetics, and analogs. Useful polymerases for ternary complex formation and detection are not limited to polymerases that have the ability to catalyze a polymerization reaction. Optionally, a useful polymerase will have the ability to catalyze a polymerization reaction in at least one condition that is not used during formation or examination of a stabilized ternary complex. Exemplary polymerases that can be used to form a stabilized ternary complex include, for example, wild type and mutant polymerases set forth in US Pat. App. Pub. Nos. 2017/0314072 A1 or 2018/0155698 A1, or U.S. patent application Ser. No. 16/567,476, which claims priority to U.S. Pat. App. Ser. No. 62/732,510, each of which is incorporated herein by reference.

Polymerases that contain an exogenous label moiety (e.g., an exogenous luminophore), which can be used to detect the polymerase, can be useful in some embodiments. Optionally, the exogenous label moiety can be chemically linked to the polymerase, for example, using a free sulfhydryl or a free amine moiety of the polymerase. An exogenous label moiety can also be attached to a polymerase via protein fusion. Exemplary label moieties that can be attached via protein fusion include, for example, green fluorescent protein (GFP), phycobiliprotein (e.g. phycocyanin and phycoerythrin) or wavelength-shifted variants of GFP or phycobiliprotein.

Polymerases can be present in a mixed-phase fluid (e.g. a fluid foam, fluid slurry or fluid emulsion) at a concentration that is at least about 1 nM, 10 nM, 100 nM, 1 µM, 10 µm, 100 µM, or more. Alternatively or additionally, the concentration of polymerases in a mixed-phase fluid can be at most about 100 µM, 10 µM, 1 µM, 100 nM, 10 nM, 1 nM or less. Polymerase concentration can be determined based on activity units (U). For example, polymerases can be present in a mixed-phase fluid at a concentration that is at least about 5 U/ml, 10 U/ml, 25 U/ml, 50 U/ml, 75 U/ml, 100 U/ml or more. Alternatively or additionally, the concentration of polymerases in a mixed-phase fluid can be at most about 100 U/ml, 75 U/ml, 50 U/ml, 25 U/ml, 10 U/ml, 5 U/ml or less.

In some configurations of the methods set forth herein, such as some nucleic acid sequencing methods, a mixed-phase fluid (e.g. fluid foam, fluid slurry or fluid emulsion) is used in some steps that employ a polymerase but not in other steps that employ a polymerase. In an exemplary configuration, a mixed-phase fluid does not contact a polymerase until after the polymerase has performed a particular function set forth herein. In this configuration, a mixed-phase fluid can optionally be used to remove the polymerase from the flow cell. A mixed-phase fluid may or may not be used to deliver a polymerase to a vessel such as a flow cell. In particular configurations, the polymerase that may or may not contact a mixed-phase fluid in one or more steps of a particular method is a labeled polymerase, a polymerase that is used to form a stabilized ternary complex or a polymerase used for primer extension. Indeed, a method can be configured such that it does not include any steps that contact a particular polymerase (or a particular type of polymerase) with a mixed-phase fluid.

A flow cell or other vessel that is used in a system or method of the present disclosure can include a nucleic acid. The nucleic acid can be in contact with a mixed-phase fluid (e.g. a fluid foam, fluid slurry or fluid emulsion) during delivery to the flow cell or during one or more steps of a method set forth herein. In some configurations, a single nucleic acid molecule is to be manipulated or detected. The nucleic acid molecule can be delivered to a vessel and can optionally be attached to a surface in the vessel. In some embodiments, the molecule is subjected to detection under conditions wherein individual molecules are resolved one from the other (e.g. single molecule sequencing). Alternatively, multiple copies of the nucleic acid can be made and the resulting ensemble can be detected or sequenced. For example, the nucleic acid can be amplified on a surface (e.g. on the inner wall of a flow cell) using techniques set forth in further detail below.

In multiplex embodiments, multiple different nucleic acid molecules (i.e. a population having a variety of different sequences) are manipulated or detected. The molecules can optionally be attached to a surface in a flow cell or other vessel. The nucleic acids can be attached at unique sites on the surface and single nucleic acid molecules that are spatially distinguishable one from the other can be detected or sequenced in parallel. Alternatively, the nucleic acids can be amplified on the surface to produce a plurality of surface attached ensembles. The ensembles can be spatially distinguishable from each other and modified, detected or sequenced in parallel.

A method set forth herein can use any of a variety of nucleic acid amplification techniques in a flow cell or other vessel. Mixed-phase fluids can be used in one or more steps of a nucleic acid amplification method set forth herein or known in the art. Exemplary techniques that can be used include, but are not limited to, polymerase chain reaction (PCR), rolling circle amplification (RCA), multiple displacement amplification (MDA), bridge amplification, or random prime amplification (RPA). Mixed-phase fluid can be used to deliver primers, templates or other amplification reagents such as those exemplified herein or in references cited herein. In particular embodiments, one or more primers used for amplification can be attached to a surface in a flow cell. In such embodiments, extension of the surface-attached primers along template nucleic acids will result in copies of the templates being attached to the surface. Such amplification methods can be used for analytical purposes such as real time PCR or quantitative PCR. Alternatively, amplification can be used to prepare nucleic acids for downstream applications such as nucleic acid sequencing. Preparative amplification methods that result in one or more sites on a solid support, where each site is attached to multiple copies of a particular nucleic acid template, can be referred to as "clustering" methods.

In PCR techniques, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a flow cell.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Primers used herein can be DNA, RNA or analogs thereof.

A nucleic acid that is used in a method or apparatus herein can be linear, for example, being flanked by 3' end and a 5' end. Alternatively, a nucleic acid can be circular, thereby lacking a 3' and 5' end. Whether linear, circular or in any other conformation, a nucleic acid that is used herein can have a size that is desired for a particular use or that is a result of manipulations carried out on the nucleic acid. For example, a nucleic acid can have a length that is at least 50 bases, 100 bases, $1\times10^3$ bases, $1\times10^4$ bases, $1\times10^5$ bases, $1\times10^6$ bases or longer. Alternatively or additionally, the nucleic acid length can be at most $1\times10^6$ bases, $1\times10^5$ bases, $1\times10^4$ bases, $1\times10^3$ bases, 100 bases, 50 bases or shorter. When a population of nucleic acids is used, the average length for the population can have a lower and/or upper limit selected from those ranges.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and detected using an apparatus or method set forth herein.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

In some configurations of the methods set forth herein, such as some nucleic acid sequencing methods, a mixed-phase fluid (e.g. fluid foam, fluid slurry or fluid emulsion) is used in some steps that employ a nucleic acid but not in other steps that employ a nucleic acid. In an exemplary configuration, a mixed-phase fluid does not contact a nucleic acid until after the nucleic acid has participated in a particular activity or step set forth herein. In this configuration, a mixed-phase fluid can optionally be used to remove the nucleic acid from the flow cell. A mixed-phase fluid may or may not be used to deliver a nucleic acid to a vessel such as a flow cell. In particular configurations, the nucleic acid that may or may not contact a mixed-phase fluid in one or more steps of a particular method is a template nucleic acid, a primer nucleic acid, a single stranded nucleic acid, a double stranded nucleic acid (e.g. a primed template nucleic acid), a 3' blocked nucleic acid (e.g. a 3' reversibly terminated nucleic acid), or a fluorescently labeled nucleic acid. Indeed, a method can be configured such that it does not include any steps that contact a particular nucleic acid with a mixed-phase fluid.

A flow cell or other vessel that is used in a system or method of the present disclosure can include an array of nucleic acids, proteins or other analytes. In particular configurations, stabilized ternary complexes are present at one or more sites of an array. The array of analytes can be in contact with a mixed-phase fluid (e.g. a fluid foam, fluid slurry or fluid emulsion) during one or more steps of a method set forth herein or in references cited herein.

Arrays provide an advantage of multiplex processing of analytes, whereby the multiple different types of analytes are manipulated or detected in parallel. Although it is also possible to serially process different types of analytes using one or more steps of the methods set forth herein, parallel processing can provide cost savings, time savings and uniformity of conditions. An array can include at least 2, 10, 100, $1\times10^3$, $1\times10^4$, $1\times10^5$, $1\times10^6$, $1\times10^9$, or more different analyte sites. Alternatively or additionally, an array can include at most $1\times10^9$, $1\times10^6$, $1\times10^5$, $1\times10^4$, $1\times10^3$, 100, 10, 2 or fewer, different analyte sites.

An array can be attached to an inner surface of a flow cell wall or to a solid support inside of a flow cell. The flow cell or solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation at that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support for use in a flow cell or other vessel is a particle such as a bead or microsphere. Populations of beads can be used for attachment of populations of analytes such as stabilized ternary complexes or components capable of forming the complexes (e.g. polymerases, templates, primers or nucleotides). In some configurations, each bead has a single type of stabilized ternary complex or a single type of component capable of forming the complex or a single type of some other analyte set forth herein or in references cited herein. For example, an individual bead can be attached to a single type of ternary complex, a single type of template allele, a single type of template locus, a single type of primer, or a single type of nucleotide. Alternatively, different types of components need not be separated on a bead-by-bead basis. As such, a single bead can bear multiple different types of: ternary complexes, template nucleic acids, primers, primed template nucleic acids and/or nucleotides. The composition of a bead can vary, depending for example, on the format, chemistry and/or method of attachment to be used. Exemplary bead compositions include solid supports, and chemical functionalities thereon, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, controlled pore glass (CPG), latex or cross-linked dextrans such as Sepharos™, cellulose, nylon, cross-linked micelles and Teflon™, as well as other materials set forth in "Microsphere Detection Guide" from Bangs Laboratories, Fishers Ind., which is incorporated herein by reference.

Beads can have a symmetrical shape, such as spherical, polyhedral, cylindrical or the like. Alternatively, beads can have an irregular or non-symmetric shape. Exemplary sizes for beads used herein can have average diameter that is at least about 10 nm, 100 nm, 1 µm, 5 µm, 10 µm, 100 µm, 1 mm or larger. Alternatively or additionally, beads used herein can have average diameter that is at most about 1 mm, 100 µm, 10 µm, 5 µm, 1 µm, 100 nm, 10 nm, 1 nm or smaller. Beads in these size ranges can be used as array features or as particles in a fluid slurry. The beads that are used as features of an array can be smaller than, larger than, or the same size as the beads that are used in a fluid slurry.

Exemplary compositions and techniques that can be used to make an array of beads include, without limitation, those used for BeadChip™ Arrays available from Illumina, Inc. (San Diego, Calif.) those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

Other useful arrays include those that are used in nucleic acid sequencing applications. For example, arrays that are used to immobilize amplicons of genomic fragments (often referred to as clusters) can be particularly useful. Examples of nucleic acid sequencing arrays that can be used herein include those described in Bentley et al., *Nature* 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid or other analyte can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more ensembles, an ensemble being a population of analytes of the same type such as a population of nucleic acids having a common template sequence. Cluster methods can be used to attach one or more nucleic acid ensembles to a solid support. As such, an array can have a plurality of ensembles, each of the ensembles being referred to as a cluster or array site in that format. Clusters can be formed using methods known in the art such as bridge amplification, emulsion PCR or other methods set forth herein.

A flow cell or other vessel that is used in a system or method of the present disclosure can include a nucleotide. The nucleotide can be in contact with a mixed-phase fluid (e.g. a fluid foam, fluid slurry or fluid emulsion) during delivery to the flow cell or during one or more steps of a method set forth herein. The nucleotide can be a native nucleotide, nucleotide analog or modified nucleotide as desired to suit a particular application or configuration of the methods. Such nucleotides can be present in a ternary complex or used in a sequencing method set forth herein.

Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that render the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Further examples of nucleotide analogs are described in U.S. Pat. No. 8,071,755, which is incorporated by reference herein.

Nucleotide analogs that are used in a method, apparatus or system herein can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be removed from a primer, in a process known as "deblocking," allowing for subsequent nucleotide incorporation. Compositions and methods for deblocking are set forth in references cited herein in the context of reversible terminators.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

In particular embodiments, nucleotide analogs that are used herein, for example, to participate in stabilized ternary complexes, do not include blocking groups (e.g. reversible terminators) that prevent subsequent nucleotide incorporation at the 3'-end of the primer after the analog has been incorporated into the primer. This can be the case whether or not an extension step is carried out using nucleotide(s) having a blocking group (e.g. reversible terminator).

In some embodiments, a nucleotide that is used herein, for example, to participate in forming a stabilized ternary complex, can include an exogenous label. An exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase.

Alternatively, a nucleotide that is used herein, for example, to participate in forming a ternary complex can lack exogenous labels (i.e. the nucleotide can be "non-labeled"). A non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful when a label on a polymerase is used to detect a stabilized ternary complex or when label-free detection is used. Non-labeled nucleotides can also be useful in an extension step of a method set forth herein. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or nucleotide analog) is present in a mixture during or after formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid. Different base types can be identifiable by the presence of different exogenous labels on the different nucleotides. Alternatively, two or more nucleotide types can have exogenous labels that are not distinguishable. In the latter format the different nucleotides can nevertheless be distinguished due to being separately delivered to a vessel or due to an encoding and decoding scheme as set forth, for example, in US Pat. App. Pub. No. 2018/0305749 A1 or U.S. Pat. No. 9,951,385, each of which is incorporated herein by reference.

Nucleotides can be present in a mixed-phase fluid (e.g. a fluid foam, fluid slurry or fluid emulsion) at a concentration that is at least about 1 nM, 10 nM, 100 nM, 1 µM, 10 µM, 100 µM, or more. Alternatively or additionally, the concentration of nucleotides in a mixed-phase fluid can be at most about 100 µM, 10 µM, 1 µM, 100 nM, 10 nM, 1 nM or less. The previous concentrations can apply to the concentration of a single type of nucleotide that occurs in the fluid or to the total concentration of two or more types of nucleotide that occur in the fluid.

In some configurations of the methods set forth herein, such as some nucleic acid sequencing methods, a mixed-phase fluid (e.g. fluid foam, fluid slurry or fluid emulsion) is used in some steps that employ nucleotides but not in other steps that employ nucleotides. In an exemplary configuration, a mixed-phase fluid does not contact particular nucleotides until after the nucleotides have participated in a particular activity or step set forth herein. In this configuration, a mixed-phase fluid can optionally be used to remove the nucleotides from the flow cell. A mixed-phase fluid may or may not be used to deliver nucleotides to a vessel such as a flow cell. In particular configurations, the nucleotides that may or may not contact a mixed-phase fluid in one or more steps of a particular method are reversibly terminated nucleotides, reversibly terminated nucleotides that have exogenous labels, reversibly terminated nucleotides that are not exogenously labeled, extendible nucleotides, extendible nucleotides that are exogenously labeled, extendible nucleotides that are exogenously labeled or other types of nucleotides set forth herein. Indeed, a method can be configured such that it does not include any steps that contact a particular nucleotide (or particular type of nucleotide) with a mixed-phase fluid.

Systems and methods of the present disclosure that employ optical detectors can further employ optically detectable labels on reactants or products that are to be detected. In many cases the labels are exogenous labels added to a reactant or product, such as a polymerase, nucleic acid or nucleotide. Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore labels include, but are not limited to rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives), Cy5 (and its derivatives) and Cy7 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610, ATTO 635; ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED, EPOCH YAKIMA YELLOW, EPOCH GIG HARBOR GREEN; Tokyo green (M. Kamiya, et al., 2005 *Angew. Chem. Int. Ed.* 44:5439-5441); and CF dyes including CF 647 and CF555 (Biotium), and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A label can be attached to a nucleotide, polymerase or other molecule via a linker. A linker that is present in a nucleotide or polymerase can be, but need not be, cleavable. For example, the linker can be stable to conditions used in methods set forth herein such that the covalent structure of the linker is not changed during any particular step, or throughout all steps, of a method set forth herein.

In alternative embodiments, a reactant or product can lack exogenous labels. For example, a stabilized ternary complex and all components participating in the stabilized ternary complex (e.g. polymerase, template nucleic acid, primer and/or cognate nucleotide) can lack one, several or all of the exogenous labels described herein or in the references that are cited and incorporated herein. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916, or U.S. Pat. App. Ser. No. 62/375,379 or Ser. No. 15/677,870, each of which is incorporated herein by reference.

A system or method of the present disclosure can use a bubble generator component to deliver gas to a liquid, thereby forming a fluid foam. The bubble generator component can be configured to deliver a population of bubbles having a desired size (e.g. measured as diameter or volume) and/or number (e.g. measured as concentration or count). In other configurations, a system can include an emulsion generator to mix immiscible liquids or a slurry generator to mix particles with a liquid.

Bubbles can have a variety of sizes including for example small nanobubbles having an effective diameter between about 1 nm and 100 nm, large nanobubbles having effective diameter larger than 100 nm and smaller than 500 nm, small microbubbles having an effective diameter between about 0.5 μm and 100 μm, large microbubbles having an effective diameter larger than 100 μm and smaller than 1 mm. Bubbles having effective diameter smaller than 500 μm, 250 μm, 100 μm, 50 μm, 40 μm, 30 μm, 20 μm, 10 μm, 5 μm, or 1 μm can be useful, for example, due to their relative stability in liquids. Bubbles that are even smaller, for example, having effective diameter smaller than 500 nm, 100 nm, 50 nm, or 10 nm can be useful due to increased stability and due to being smaller than the wavelengths of light typically used for luminescence detection. Alternatively or additionally to these exemplary upper limits, bubbles can have an effective diameter that is larger than 10 nm, 50 nm, 100 nm, 500 nm, 1 μm, 5 μm, 10 μm, 25 μm, 50 μm, 100 μm, 250 μm or 500 μm, as exemplary lower limits. A population of bubbles can have an average diameter, average effective diameter, maximum diameter or minimum diameter that is delineated by one or both of the upper and lower limits exemplified above. Other mixed-phase fluids can contain particles or globules that are in the same or similar size ranges as those exemplified above for bubbles.

It will be understood that the 'effective' diameter of a bubble is a measure of the bubble in a spherical state. If the bubble is a pancake (e.g. squashed by the walls of a flow cell) or other shape, the effective diameter of the pancake bubble will be understood to be a measure of the diameter of the bubble when it is converted to a spherical state of the same volume. Similarly, the 'effective' diameter of a globule is a measure of the globule in a spherical state. If the globule is a pancake (e.g. squashed by the walls of a flow cell) or other shape, the effective diameter of the pancake globule will be understood to be a measure of the diameter of the globule when it is converted to a spherical state of the same volume.

In particular configurations, the bubbles in a fluid foam can have an average diameter, maximum diameter or minimum diameter that is measured relative to the dimensions of a detection channel at a particular region of detection in a flow cell. Generally, it is preferable for the bubbles to be smaller than the detection channel of a flow cell through which the bubbles will flow. For example, the average effective diameter, maximum effective diameter or minimum diameter of the bubbles can be at most 99%, 95%, 90%, 75%, 50%, 25%, 10%, 5%, 1%, 0.1% or 0.01% or less of a relevant dimension of the detection channel region. Alternatively or additionally, the average effective diameter, maximum effective diameter or minimum effective diameter of the bubbles can be at least 0.01%, 0.1%, 1%, 5%, 10%, 25%, 50%, 75%, 90%, 95%, 99% or more of the relevant dimension of the detection channel at the point of detection. The relevant dimension can be, for example, the width of the channel (e.g. the x dimension, wherein the y dimension is the direction of fluid flow and the z dimension is the depth of the channel or the focus dimension for optical detection through the channel). The relevant dimension can be the depth of the channel in the z dimension or the relevant dimension can be along the y dimension. Other mixed-phase fluids can contain particles or globules that are in the same or similar size ranges as those exemplified above for bubbles.

In some configurations, a bubble can form a bolus or slug that occupies the full cross-sectional area of a flow cell channel where the bubble resides. A bubble slug or bolus can be useful to clear a particular fluid from a flow cell, such as a fluid that carries one or more of the reagents or analytes that occur in a method set forth herein. As such, different liquids that are delivered to a flow cell can be separated by a bubble slug or bolus. Although the cross-sectional area of the flow cell will confine the maximum cross-sectional area of the bubble bolus or slug, larger bubbles will be accommodated by being deformed by the channel. As the volume of the bubble increases, the length of the channel that the bubble occupies will increase. For example, a bubble bolus or slug can have a volume that in a non-deformed state (i.e. spherical shape) would have a maximum cross-sectional area that is at least 1×, 2×, 5×, 10× or 100× larger than the cross-sectional area of the channel where it resides. Bubble slugs having larger volumes can provide increased physical separation of two fluids. This can provide advantages of reducing precision required for detection or fluid delivery steps. Smaller volume bubble slugs can provide for separation of fluids while reducing the time that the flow cell surface is exposed to gas. This reduced exposure can be beneficial when an array, or other active flow cell surface, is sensitive to drying or other effects from exposure to gas. A globule of liquid can form a slug or bolus having similar sizes and properties as those exemplified for bubbles.

In some configurations, a bubble bolus can be used to clear all or part of a common fluid line that is upstream of a flow cell or other vessel. A bubble bolus can provide relatively rapid exchange of one fluid reagent for another in the common fluid line since the bubble bolus drives out the first fluid and physically separates the two fluids to inhibit cross contamination that would occur if the two fluids were in contact while in the common fluid line. A bubble bolus can be delivered to a common line, flow cell or other fluidic component using a bubble generator. An exemplary method is set forth below in the context of FIG. 6.

A population of bubbles, globules or particles in a mixed-phase fluid can be monodisperse or polydisperse. Monodisperse populations will have uniform sized bubbles, globules or particles, for example, the size coefficient of variation (CV) being no more than 10%. In some configurations an even tighter uniformity can be useful including, for example, the size CV being no more than 1% or 5% from the mean. The size CV for a polydisperse population of bubbles, globules or particles can range, for example, from greater than 10% to at most about 25%, 50%, 100%, 2-fold, 5-fold, 10-fold, 100-fold or more. In some situations, a relatively high degree of polydispersity occurs and as such the size CV for the bubbles, globules or particles can be at least about 25%, 50%, 75%, 100%, 2-fold, 5-fold, 10-fold, 100-fold or more. The sizes of the bubbles, globules or particles in a polydisperse population can range, for example, within a range set forth above.

The concentration of gas bubbles in a fluid foam can be selected for a particular application. In some cases, the concentration of gas bubbles in a fluid foam can be controlled by a bubble generator component. For example, the concentration (i.e. volume fraction) of bubbles in a fluid foam can be at least 0.01%, 0.1%, 1%, 5%, 10%, 25%, 50%, 75%, 90% 95%, 99% or more of the total volume of the fluid foam in a particular vessel such as a detection channel of a flow cell. Increasing the volume fraction of bubbles in a fluid can provide an advantage in reducing reagent consumption without necessarily reducing the effective concentration of the reagent in the foam compared to in the original liquid reagent. This can provide a reduction in cost especially when using relatively expensive reagents. Example 1, below, provides a demonstration of reagent savings due to introduction of bubbles into various reagent solutions used for nucleic acid sequencing. Another advantage of increasing the concentration of bubbles in a fluid foam is the concomitant reduction in the volume of liquid to be shipped, stored, discarded or otherwise handled. An example can illustrate these advantages. A nucleic acid sequencing method that consumes 100 ml of liquid polymerase solution can be configured to consume only 50 ml by introducing bubbles into the liquid to create a foam that is 50% bubbles and 50% liquid polymerase solution. In another example, bubbles can be introduced into a liquid reagent to increase the number of analytes that are processed by the same volume of liquid reagent. More specifically, a nucleic acid sequencing method that consumes 100 ml of liquid nucleotide solution, to sequence arrayed nucleic acids in one lane of a flow cell, can be modified to sequence 2 lanes of the flow cell by introducing bubbles into the 100 ml volume of liquid nucleotide solution to create a 200 ml volume of fluid foam that is 50% bubbles and 50% liquid nucleotide solution. Increasing the foam to a 75% bubble fraction can allow 4 lanes to be sequenced since 400 ml of nucleotide solution will be produced at the same effective concentration as the original nucleotide solution.

As an alternative or addition to the optional lower limits exemplified above, the concentration of bubbles in a fluid foam can be at most 99%, 95%, 90%, 75%, 50%, 25%, 10%, 5%, 1%, 0.1% or 0.01% or less of the total volume of the fluid foam in a particular vessel such as a detection channel of a flow cell. Reducing the bubble fraction can provide for delivery of a larger amount of a particular reagent in the same volume of fluid. Taking a nucleic acid sequencing method as an example, later cycles of the method may benefit from a larger quantity of polymerase reagent compared to earlier cycles due to a reduction in signal to noise that occurs over the course of the method. In this example, the fraction of bubbles can be increased over the course of the method such that the polymerase fluid is introduced to a flow cell with few to no bubbles and later cycles have a larger bubble fraction. Reduction of bubble fraction can be particularly advantageous when a substantial amount of the reagent in the fluid is consumed (e.g. when using a quantity of reagent that is subsaturating in the method of use) because removal of bubbles will result in a fluid having an increase in the effective amount of reagent in a given fluid volume. Other mixed-phase fluids can contain particles or globules that are in the same or similar concentration ranges, or in the same fluid fraction ranges, as those exemplified above for bubbles.

A bubble generator can be configured to deliver fluid foams having a variety of bubble sizes, bubble concentrations or bubble polydispersities, for example, in the ranges exemplified above. Alternatively or additionally, a bubble generator component can be configured to deliver a desired number of bubbles. For example, the bubble generator component can produce or deliver bubbles at a rate of at least 1 sec$^{-1}$, 5 sec$^{-1}$, 10 sec$^{-1}$, 50 sec$^{-1}$, 100 sec$^{-1}$, 250 sec$^{-1}$, 500 sec$^{-1}$ or more. Alternatively or additionally, the rate of bubble production or delivery can be at most 500 sec$^{-1}$, 250 sec$^{-1}$, 100 sec$^{-1}$, 50 sec$^{-1}$, 10 sec$^{-1}$, 5 sec$^{-1}$, 1 sec$^{-1}$, or lower. Again, a bubble generator component of the present disclosure can be configured to generate a population of bubbles having a number of bubbles in a range exemplified above, and having bubble size in a range exemplified above. The rate of delivery for liquid globules or particles in a mixed-phase fluid can be in a range exemplified above for bubbles.

An exemplary bubble generator component that can be used to make a fluid foam is shown in FIG. 1. Flow cell 100 includes two detection channels 110 and 120 along with bubble generator components that are integrated into the flow cell substrate 101. The detection channels can optionally have a length of a few centimeters to several centimeters (in the direction of flow), a width of a few microns to several millimeters and depth of few microns to several millimeters. For brevity, the fluidic pathways through detection channels 110 and 120 will be described together with reference to channel 120 in parentheses. Liquid enters inlet 115 (125) and passes through liquid channel 114 (124) to a T junction 113 (123) that forms with gas channel 116 (126), the gas having entered the system via inlet 117 (127). The gas channel 116 (126) has a cross sectional area that is smaller than the detection channel 110 (120). The gas channel optionally is circular with a diameter between about 1 micron and 200 microns, but can be larger in other configurations, for example, up to 500 microns. The T junction can have a narrowed point to form a venturi where gas and liquid mixes to form a fluid foam. The fluid foam then passes through the channel to enter detection channel 110 (120) via connection 112 (122). The fluid foam then exits the detection channel 110 (120) through egress 111 (121).

Figure 2:
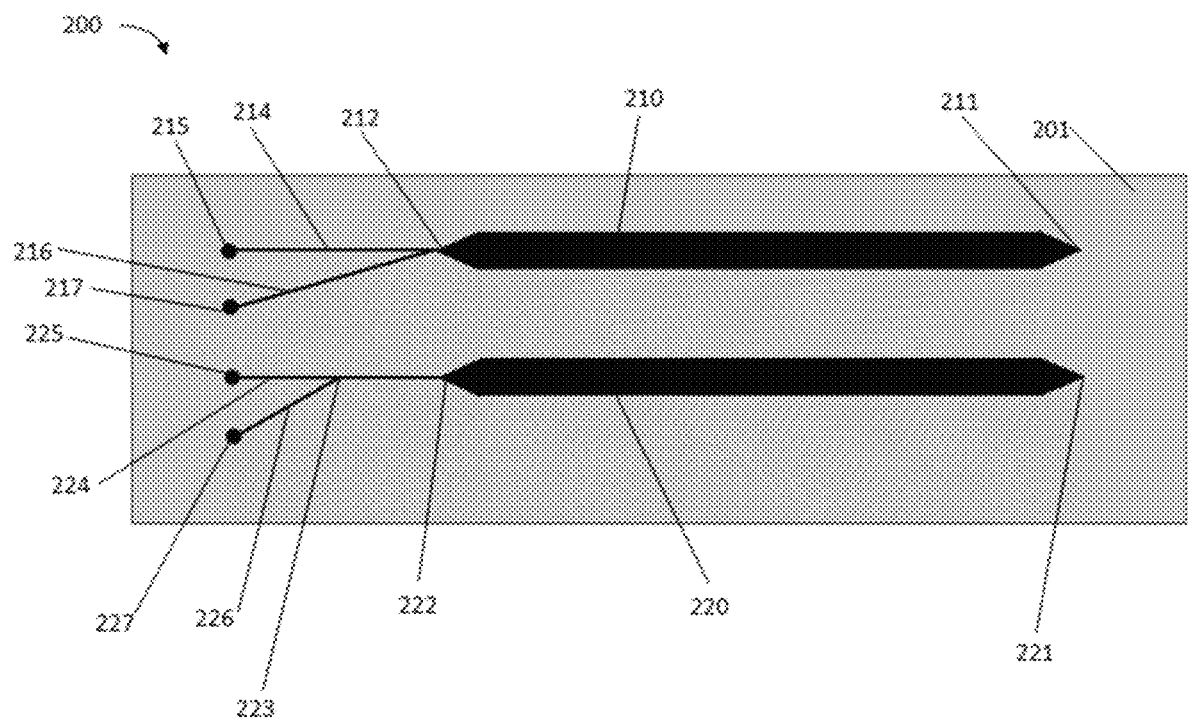
FIG. 2 shows a flow cell having two detection channels, each of the detection channels being fluidically connected to a gas mixing component, the gas mixing component using a Y junction to connect a liquid channel and a gas channel.

An alternatively configured flow cell is shown in FIG. 2. Flow cell 200 includes two detection channels each of which is fed a fluid foam from a phase mixing component that is integrated into the flow cell substrate 201. The upper detection channel 210 is fed fluid foam via a phase mixing component that has a Y junction 212 at the opening of the detection channel 210. As such, liquid enters ingress 215 and flows through channel 214 to the Y junction 212 where it mixes with gas that has entered the flow cell via ingress 217 and then flows along channel 216 to enter the Y junction 212. The fluid foam then passes through detection channel 210 and exits via egress 211. The lower detection channel 220 is fed fluid foam via a phase mixing component that has a Y junction 223 upstream of the opening 222 of the detection channel 220. As such, liquid enters ingress 225 and flows through channel 224 to the Y junction 223 where it mixes with gas that has entered the flow cell via ingress 227 and along channel 226 to the Y junction 223. The fluid foam then passes through the remainder of fluid channel 224, into detection channel ingress 222, through detection channel 220 and exits via egress 221.

The Y junctions in flow cell 200 are formed from inlet channels that meet at an acute angle. For example, the fluid channels 214 and 216 form an acute angle at Y junction 212. The angle is relatively small compared to the acute angle formed by intersection of channels 226 and 224 at Y junction 223. The angle can be adjusted to produce desired characteristics for the fluid foam such as average bubble size and bubble count (i.e. concentration of bubbles).

Figure 3:
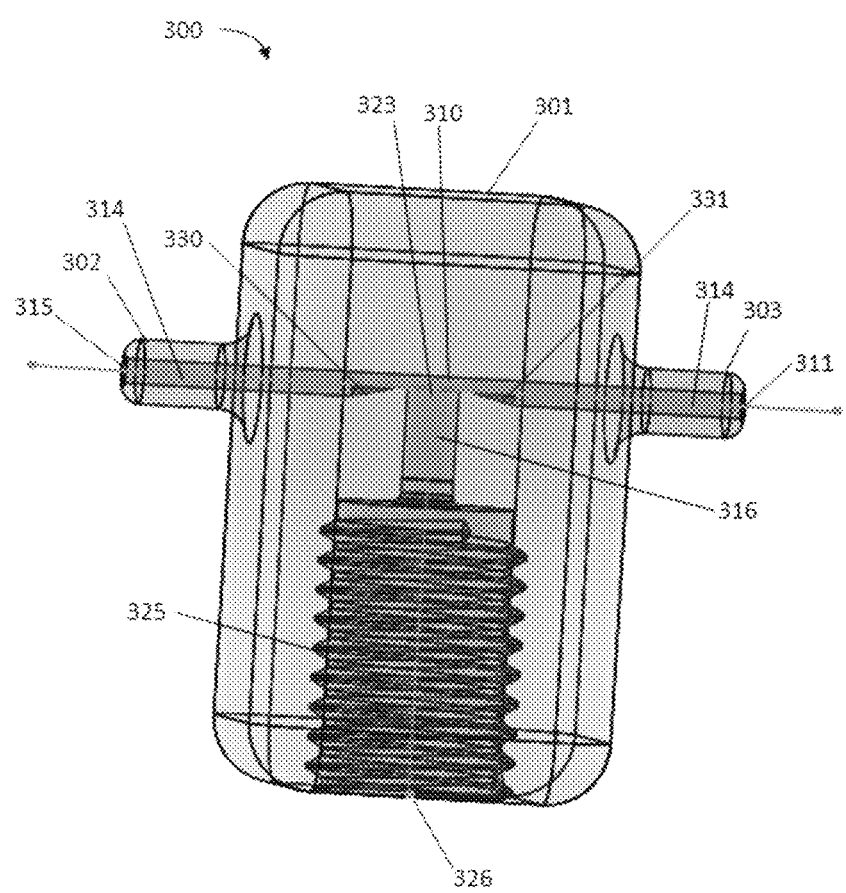
FIG. 3 shows a bubble generator having a T junction and a threaded coupling for a gas line.

As exemplified by the apparatus shown in FIGS. 1 and 2, a bubble generator can be an integral part of a flow cell or other vessel. In alternative configurations, a bubble generator can be a separate or separable component relative to a flow cell or other vessel. An example of a bubble generator 300 that is separable from other fluidic components is shown in FIG. 3. Bubble generator 300 includes a body 301 having internal plumbing that is accessed by liquid inlet 315, gas inlet 326 and foam outlet 311. A straight channel 314 connects liquid inlet 315 to foam outlet 311. Gas inlet 326 connects to channel 314 via channel 316, the two channels forming a T junction 323. Gas flowing from gas inlet 326 can be introduced to liquid flowing from liquid inlet 315 at T junction 323 to form a fluid foam that flows out foam outlet 311. Channel 314 narrows at locations 330 and 331 to create narrowed region 310. The T junction 323 occurs in the narrowed region 310 of straight channel 314. A gas source can be connected to bubble generator 300 via threaded coupling 326. The threads 325, being internal, form a female fitting that is configured to accept a threaded male connector for a gas line. It will be understood that connection of a gas line to the bubble generator 300 can employ opposite fittings (i.e. male fitting on the bubble generator and female fitting on the gas line) or non-threaded fittings. For example, connection can employ pressure fitting, pipe fitting, adhesive-mediated fitting, clamping or other fittings known in the arts of fluidics and plumbing. A liquid line can be connected to inlet 315 via fitting 302. For example, fitting 302 forms a male fitting that can insert into a flexible tube to create a connection. Similar connection can be made for fitting 303 to transfer foam from egress 311 to a flow cell or other fluidic component.

Figure 4:
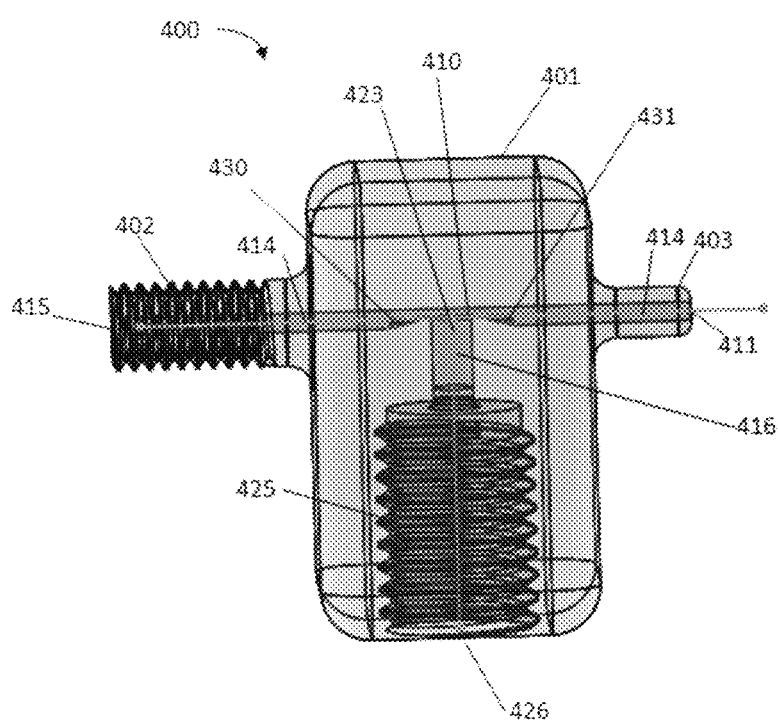
FIG. 4 shows a bubble generator having a T junction, and threaded couplings for a gas line and a liquid line.

FIG. 4 shows a bubble generator 400 having body 401 and an internal T junction 423 that is configured similarly to the one shown in FIG. 3. T junction 423 connects channel 414 with channel 416 such that gas introduced via gas inlet 426 can combine with liquid introduced from liquid inlet 415 to create a foam that flows out foam outlet 411. Channel 414 narrows at locations 430 and 431 to create narrowed region 410. The gas inlet fitting 426 and foam outlet fitting 403 are similar to those in FIG. 3. A gas source can be connected to bubble generator 400 via threaded coupling 426. The threads 425, being internal, form a female fitting that is configured to accept a threaded male connector for a gas line. The fitting 402 for the liquid inlet is a male, threaded fitting. The threaded fitting can provide for convenient connection to a fluid line; however, other types of fittings can be used instead such as those exemplified above in the context of FIG. 3.

A bubble generator need not necessarily employ a T junction (i.e. where a gas carrying channel intersects a linear channel at an orthogonal angle, the linear channel having a fluid ingress at one end and a foam egress at the other end). Rather, channels can intersect at non-orthogonal angles. The angle of intersection can be configured to achieve desired properties of a foam for a particular use. In another alternative, a T junction can be configured such that a liquid-carrying channel intersects a linear channel at an orthogonal angle, the linear channel having a gas ingress at one end and a foam egress at the other end.

Figure 5:
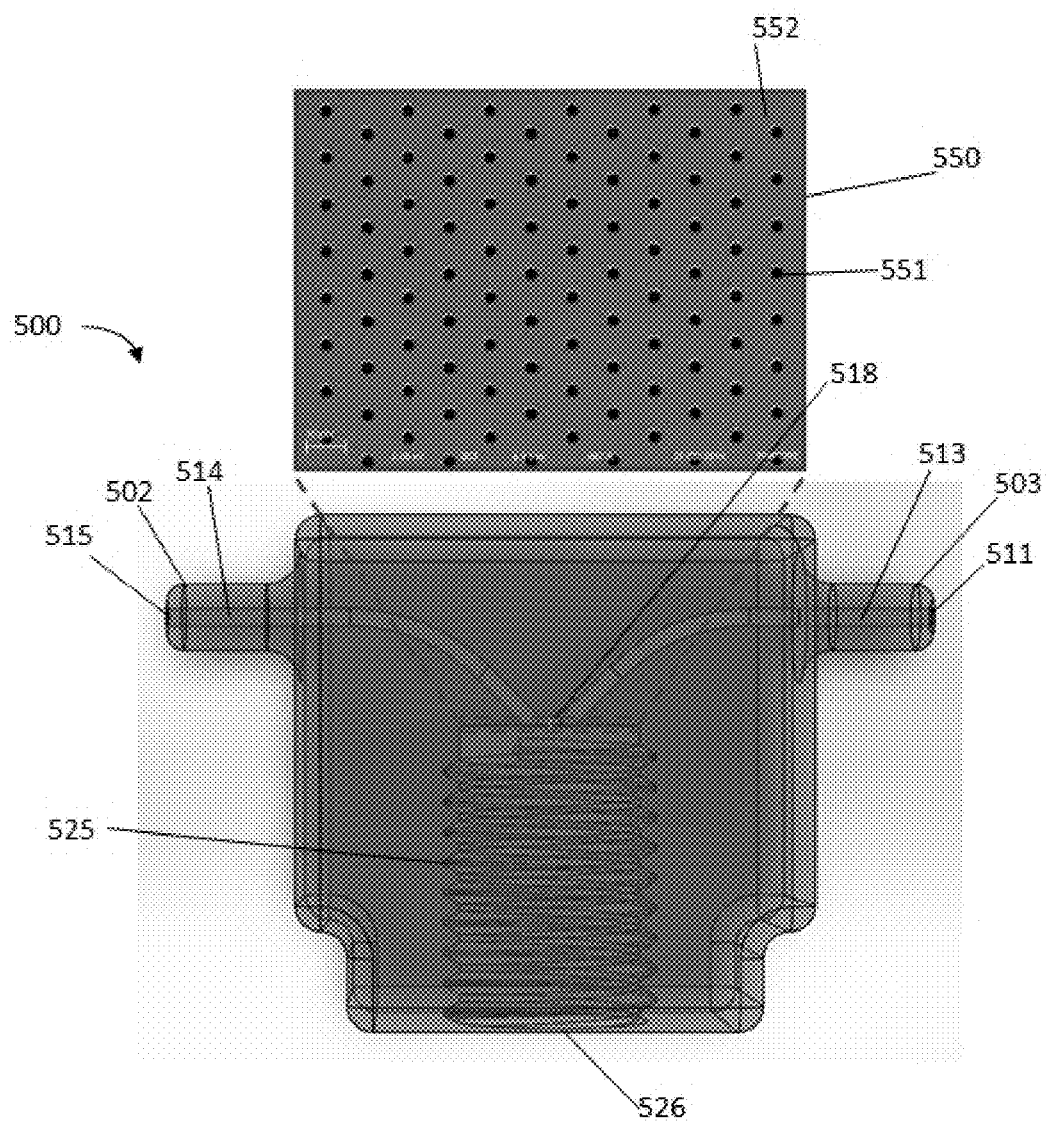
FIG. 5 shows a bubble generator having a Y junction and a hydrophobic filter membrane that functions as a gas resistor at the junction.

FIG. 5 shows a bubble generator 500 having a Y junction 518. Gas flows to Y junction 518 from gas inlet 526, where it contacts liquid flowing through channel 514 from liquid inlet 515. The resulting foam flows through channel 513 and out foam outlet 511. Channels 514 and 513 are curved but can be linear. Bubble generator 500 includes a threaded female fitting 525 for gas inlet 526, a non-threaded male fitting 502 for the liquid inlet 515 and a non-threaded male fitting 503 for the foam outlet 511. Bubble generator 500 includes a filter membrane 550 having a pattern of holes 551 in a hydrophobic material 552 that functions as a gas diffuser. The membrane 550 can be placed within the barrel of gas inlet 526.

The membrane 550 shown in FIG. 5 is exemplary. The membrane is configured to function as an array of holes that experiences a Young-Laplace pressure drop. The Young-Laplace equation is a nonlinear partial differential equation that describes the capillary pressure difference sustained across the interface between two static fluids, such as a liquid and a gas, due to the phenomenon of surface tension. The equation can also describe the capillary pressure difference sustained across the interface between two static fluids due to the phenomenon of wall tension if the wall is very thin. The Young-Laplace equation relates the pressure difference to the shape of the surface or wall. It is a statement of normal stress balance for static fluids meeting at an interface, where the interface is treated as a surface (zero thickness):

$$\Delta p = -\gamma \nabla \cdot \hat{n}$$
$$= 2\gamma H$$
$$= \gamma \left( \frac{1}{R_1} + \frac{1}{R_2} \right)$$

For Equation 1 above, $\Delta p$ is the Laplace pressure, the pressure difference across the fluid interface; $\gamma$ is the surface tension (or wall tension), $\hat{n}$ is the unit normal pointing out of the surface, H is the mean curvature, and $R_1$ and $R_2$ are the principal radii of curvature. The Young-Laplace equation can also be used for creating or evaluating emulsions. Membrane 550, or a similar apparatus, can be used in other bubble generators set forth herein including, for example, those employing structural or functional elements shown in FIGS. 1 through 4.

The membrane thickness can be any that achieves the desired characteristics for the mixed phase fluid. For example, the membrane can have a thickness of at least 100 nm, 500 nm, 1 µm, 10 µm, 100 µm, 500 µm or thicker. The upper limit of membrane thickness can be determined based on desired characteristics of the mixed phase fluid. For example, as an alternative or addition to the exemplary lower end of the range set forth above, the thickness can be at most 500 µm, 100 µm, 10 µm, 1 µm, 500 nm, 100 nm or less. Of course, the use of a membrane is an option. In some configurations the phase mixing component can lack a membrane.

As an alternative or addition to adjusting membrane thickness, the number, size, and pitch of the holes in the membrane can be adjusted to provide a foam or emulsion having desired properties. Generally, a hole size between 1 micron and 80 microns can be useful for providing a means to control bubble fraction or droplet fraction via differences in gas pressure and oil flow rate, respectively. For example, changing gas pressure in the range of 15 to 50 psi for gas passing through a membrane with 1 µm holes provides control of bubble fraction and polydispersity. When the membrane has 5 µm holes instead, the range of gas pressure that provides control of bubble fraction and polydispersity is 5 to 30 psi. Although a membrane having 80 µm holes is capable of producing bubbles, the bubble fraction and polydispersity will be less responsive to changes in gas pressure.

Accordingly, membranes having holes smaller than about 80 microns are generally preferred, for example, in configurations where variable control of foam or emulsion characteristics is desired. Larger hole sizes can be used when variability in foam or emulsion characteristics is to be minimized.

The average pitch for a collection of holes in a membrane can be any of a variety of lengths including, for example, at least 1 µm, 5 µm, 10 µm, 25 µm, 50 µm, 100 µm or more. Alternatively or additionally, the pitch for the hole sin particular membrane can optionally be at most 100 µm, 50 µm, 25 µm, 10 µm, 5 µm, 1 µm or less. Generally increasing the pitch for the holes can provide increased responsiveness of bubble fraction (or droplet fraction) and polydispersity to the pressure of the gas being applied (or to the flow rate of the oil being applied). Decreasing the pitch may be desirable when less variability in emulsion and foam characteristics is desired.

Other properties of the membrane can also affect characteristics of the foam or emulsion. For example, a hydrophobic material is generally preferred for the membrane. Exemplary materials that can be used for the membrane include, but are not limited to, polycarbonate and polytetrafluoroethylene (PTFE). Another exemplary characteristic is the surface area of the membrane. A larger surface area between the gas phase and liquid phase has been observed to provide greater control of gas fraction and bubble polydispersity in a foam generator. The area for a membrane that is used to produce a foam or emulsion can be at least about 10 µm², 50 µm², 100 µm², 500 µm², or 1 mm² or more. Alternatively or additionally, the area for a membrane that is used to produce a foam or emulsion can be at most about 1 mm², 500 µm², 100 µm², 50 µm², 10 µm², or less.

The gas resisting membranes set forth above are optional and need not be used. Whether a gas resisting membrane is used or not. The size of the air inlet that intersects the liquid line at a phase mixing junction can be from a few microns in size up to several hundred microns. For example, the junction for a phase mixing apparatus can have a cross section that is in the ranges set forth above for the surface area of the membranes set forth above.

The mixing systems exemplified in FIGS. 1 through 5, or modified versions thereof, can be used for producing a fluid emulsion or fluid slurry. For example, the gas channel can be used to deliver a second fluid that is immiscible with the liquid in the liquid line, thereby producing an emulsion. In another example, the gas channel can be used to deliver particles, for example, in a carrier fluid, thereby producing a fluid slurry.

Any of a variety of bubble generator systems can be used for generating bubbles such as those set forth in Garstecki et al., *Bulletin of the Polish Academy of Sciences* 53: 361-372 (2005), which is incorporated herein by reference. In particular configurations, a channel junction can be used to introduce gas bubbles into a liquid. In this geometry the gas is fed into a main channel that carries the liquid. The liquid wets the walls of the channel preferentially, and as the gas phase enters the main duct, it breaks into bubbles. Another exemplary bubble generator uses geometries in which liquid is forced through a narrow constriction in the main channel, and the gas—dispensed from a nozzle located closely upstream of the constriction—is focused into this orifice by the converging streamlines of the liquid. Useful bubble generators include those known in the art as bubble injectors, emulsifiers (e.g., ultrasonic emulsifiers), venturi injectors and bubble diffusers.

In some configurations, a mixed-phase fluid can be formed in a fluidic system at a location that is downstream of a liquid reservoir (e.g. a liquid reservoir containing a nucleic acid sequencing reagent) and upstream of a vessel used for analytical detection or synthetic reaction (e.g. flow cell containing an array of nucleic acids to be sequenced). This configuration provides an advantage of avoiding relatively large reservoirs to accommodate the mixed-phase fluid volume compared to the volume of the liquid phase alone. Introducing a dispersed phase downstream of a reservoir can also reduce damage to a reagent that is sensitive to the material of the dispersed phase. As such, the half-life of the sensitive reagent can be increased compared to a configuration where the reagent would have been maintained in a reservoir where it is in contact with the dispersed phase. In alternative configurations, bubbles can be introduced into reservoirs that contain various liquids to produce fluid foam in the reservoirs prior to transferring the liquids out of the reservoir.

A bubble generator component can be configured to adjust one or more of the following parameters to produce a fluid foam having desired properties. Bubble size, stability, polydispersity and number can be selected by adjusting the pressure applied to the gas stream, the rate of flow of the liquid, the dynamic viscosity of the liquid and/or the interfacial tension between the two phases. The pressure applied to the gas stream can be adjusted by a gas flow regulator or by a valve. The geometry of the gas line, geometry of the liquid line, geometry of the junction between the lines and/or the relative rate of gas flow and liquid flow through the lines can also be adjusted to influence bubble size, stability and number. Similarly, the size, number, polydispersity and stability of globules in a fluid can be selected by adjusting the flow rates of the two phases, the dynamic viscosity of the phases and/or the interfacial tension between the two phases in a phase mixing component.

The flow of liquid can be adjusted by adjusting the force (e.g. pressure or fluid displacement force) applied to the liquid and/or via a valve. Flow rate ranges can optionally be in the range of 10 µl/s to 100 µl/s. A slower flow rate for a particular liquid phase can be used to produce a fluid foam having a relatively high volume fraction ratio of gas to liquid, and the flow rate for the liquid phase can be increased in order to produce a foam having a lower volume fraction ratio of gas to liquid. A gas stream can be turned on and off to produce a fluid foam or non-foam fluid, respectively. It has been observed that fluid foam will produce increased back pressure as the gas fraction in the foam increases. The relationship between gas fraction and backpressure can produce a stabilizing effect. In this regard, increased back pressure decreases gas flow rate which decreases the gas fraction which decreases the back pressure. This inverting circle of interactions can be exploited as a negative feedback which stabilizes the gas flow rate (and bubble fraction).

Similarly, the flow of immiscible liquid or particles can be turned on to produce a fluid emulsion or fluid slurry and turned off to deliver a single-phase liquid. As such, a phase mixing component or bubble generator component can be configured to pass liquids from any of a variety of reservoirs in a system to the flow cell, whether or not the liquids will be converted to a mixed-phase fluid prior to entering the flow cell. In an alternative configuration, liquids that are to be converted to a mixed-phase fluid pass through the phase mixing component or bubble generator component, whereas liquids that will not be converted to a mixed-phase fluid are routed to the flow cell without passing through the phase mixing component or bubble generator component.

A mixed phase fluid can flow into and out of a flow cell in a single direction. Alternatively, the mixed phase fluid can be toggled in and out of a flow cell, for example, to achieve mixing or to dislodge unwanted materials. Toggling can be achieved by changing the direction of force (e.g. pressure or fluid displacement force) placed on the mixed phase fluid. For example, a single pressure source can alternative from applying positive pressure to applying negative pressure at a particular point in the fluidic system. Similarly, a fluid displacement apparatus can alternative from displacing fluid in a first direction to displacing fluid in the opposite direction at a particular point in the fluidic system. Alternatively, two or more sources for applying pressure or fluid displacement can be used. For example, a first pump can apply pressure or fluid displacement to the fluidic system on a first side of the flow cell and a second pump can apply pressure or fluid displacement to the fluidic system on a second side of the flow cell. The pumps can apply positive pressure, negative pressure or both. Toggling can be achieved by alternately applying positive pressure from both pumps or, conversely, toggling can be achieved by alternately applying negative pressure from both pumps. Similarly, toggling can be achieved by alternately displacing fluids in opposing directions from both pumps. An example of toggling (also referred to as 'wiggling') of a fluid foam is provided in Example 1, below.

A system of the present disclosure can include a heater or chiller that is configured to control the temperature of a material that is used to produce a dispersed phase in a mixed-phase fluid. For example, a heater can be used to raise the temperature of a gas that is used to produce bubbles in a fluid foam, a liquid that is used to produce droplets in a fluid emulsion or particles that are used to produce a fluid slurry. The heated dispersed phase will have high contact area with the bulk phase and as such can be quite efficient at heating the bulk phase. In other examples, a chiller can be used to lower the temperature of a gas that is used to produce bubbles in a fluid foam, a liquid that is used to produce droplets in a fluid emulsion or particles that are used to produce a fluid slurry. Again, due to high contact area between the dispersed phase and the bulk phase, cooling can be achieved efficiently.

A heater or chiller can be positioned to control temperature of the materials when they are present in a fluid reservoir, fluid delivery channel, vessel or other fluidic component. In particular configurations, the location of heating or chilling can be downstream of a fluid reservoir and upstream of a phase mixing component. Alternatively or additionally, heating or chilling can occur at the location where phase mixing occurs (i.e. at the location of the phase mixing component). As such, a liquid reagent can be stored in a reservoir at a first temperature (e.g. a temperature that provides stability) and the temperature of a subfraction of the reagent can be altered later for use in a downstream process.

When the desired temperature for a mixed-phase fluid is higher than the temperature of the liquid phase from which it is formed, the material that will form the dispersed phase (e.g. gas, solid or immiscible liquid) can be heated to a temperature that is higher than the desired temperature. For example, the heater can have a set point that is at least about 5° C., 10° C., 15° C. or higher than the desired temperature of the fluid in a downstream flow cell. More specifically, the heater that is upstream of the flow cell can have a set point that is higher than the set point for a heater or chiller that regulates the temperature of the flow cell. The temperature differential can be selected to account for cooling that may happen for the mixed-phase fluid while it travels to the flow cell. The temperature differential can be selected based on the heat capacity of the mixed-phase, the level of insulation for the fluidic components, the temperature differential between ambient temperature and the flow cell, and the time for the mixed-phase fluid will spend between heating and use in the flow cell.

When the desired temperature for a mixed-phase fluid is lower than the temperature of the liquid phase from which it is formed, the material that will form the dispersed phase (e.g. gas, solid or immiscible liquid) can be chilled to a temperature that is lower than the desired temperature. For example, the chiller can have a set point that is at least about 15° C., 10° C., 5° C. or lower than the desired temperature of the fluid in a downstream flow cell. More specifically, the chiller that is upstream of the flow cell can have a set point that is lower than the set point for a heater or chiller that regulates the temperature of the flow cell. The temperature differential can be selected to account for heating that may happen for the mixed-phase fluid while it travels to the flow cell. The temperature differential can be selected based on properties similar to those exemplified above for heating.

In some configurations, the liquid phase that will form the bulk phase (e.g. the liquid phase that carries reagents, analytes or the like) can be heated or chilled. Alternatively or additionally, a mixed-phase fluid can be heated or chilled downstream of a phase mixing component including, for example, in fluidic lines that deliver the mixed phase fluid to a flow cell and/or in the lanes of a flow cell or other vessel.

Heating or chilling can be achieved using any of a variety of heat transfer mechanisms including, but not limited to, Joule heating, convection, Peltier control, or radiation. Apparatus and systems for heating or chilling fluids upstream of a flow cell and that can be modified for use with mixed-phase fluids are set forth in U.S. Pat. App. Ser. No. 62/782,565, which is incorporated by reference herein.

Valves, heaters, chillers or other elements of a phase mixing component or bubble generator component can be controlled by a control module. Exemplary configurations for a control module are set forth in further detail below. By way of example, the control module can be programmed to open a valve to allow gas, a dispersable liquid or particles to mix with a dispersion liquid, thereby delivering a mixed-phase fluid to the flow cell and the control module can also be programmed to close the valve to deliver a single-phase fluid to the flow cell. In this example, the mixed-phase fluid can contain a reagent that modifies nucleic acids during a sequencing reaction. This fluid can be removed and replaced by the single-phase (e.g. non-foam, non-emulsion or non-slurry) fluid to allow optical detection of the nucleic acid. Removal of bubbles, globules or particles improves detection accuracy by avoiding optical scattering that would occur in the mixed-phase fluid.

The interior surfaces of the fluidic lines in the bubble generator component and the flow cell channel can be hydrophilic or hydrophobic. The surface can thus be adjusted to reduce or prevent bubbles, globules or particles from sticking to the surfaces. When using aqueous liquid it can be beneficial to use components (e.g. flow cells and tubes) having hydrophilic surfaces. Hydrophilicity helps to prevent bubbles from attaching to the surfaces. Surfactants can be included in a foam to further inhibit bubbles from attaching to surfaces. Particularly useful surfaces are made from cyclic olefin copolymer (COP) which demonstrates useful hydrophilic character when in contact with aqueous solutions that contain surfactants.

Liquids can be delivered to a phase mixing component, bubble generator component and/or flow cell under pressure or other fluid displacing force. Typically, liquids are delivered under positive pressure or positive fluid displacement (e.g. pushing force), but in some configurations negative pressure or negative fluid displacement (e.g. pulling force) can be used. Useful pumps include, for example, those that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps peristaltic pumps, and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); gravity; electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential.

The liquids that are used in a method or system set forth herein can be formulated to include desired reactive reagents including, for example, those set forth below in the context of sequencing processes. The liquid reagents can be stored in reservoirs. For example, one or more reservoirs in a system set forth herein can contain polymerases, nucleotides, nucleic acids, deblocking reagents, polymerase cofactors, polymerase inhibitors, ternary complex stabilizing agents or the like.

One or more of the liquids can further contain surfactants, for example, to inhibit bubbles, particles or globules from coalescing when the liquid is used to produce a mixed-phase fluid. Surfactants can be anionic, cationic, non-ionic or zwitterionic. Exemplary surfactants include, but are not limited to, sodium dodecyl sulfate (SDS), Tween-20 (polysorbate 20), Tween-80 (polysorbate 80), cetrimonium bromide, cetyltrimethylammonium bromide, Triton X-100, CHAPS, or NP-40. Amphoteric surfactants such as betaines or sulfobetaines can be useful. Surfactants can help to stabilize bubbles in a fluid foam. Surfactants can also help stabilize other components of a foam, or other mixed-phase fluid, such as proteins or nucleic acids. A relatively low concentration of surfactant can be useful in a mixed-phase fluid. For example, a mixed-phase fluid can contain at least 0.005%, 0.01%, 0.05%, 0.1%, 0.5%, 1%, 5% or more surfactant. For some uses, the amount of surfactant will be limited, for example, to prevent unwanted interactions with other component in a mixed-phase fluid. For example, the concentration of surfactant in a mixed fluid phase fluid can be at most 5%, 1%, 0.5%, 0.1%, 0.05%, 0.01%, 0.005% or less surfactant.

Alternatively or additionally to the presence of surfactants, one or more of the liquids can contain solutes that increase or decrease viscosity. For example, viscosity can be increased by addition of polyols or sugars such as glycerol, erythritol, agarose, arabitol, sorbitol, mannitol, xylitol, mannisdomannitol, glucosylglycerol, glucose, fructose, sucrose, trehalose, methylcellulose, hydroxyethylcellulose, carboxymethylcellulose, microcrystalline cellulose, xanthan gum, (+)-arabinogalactan (e.g. from Larch wood), maltodextrin (dextrose equivalent 4.0-7.0), maltodextrin (dextrose equivalent 13.0-17.0), maltodextrin (dextrose equivalent 16.5-19.5), locust bean gum, carrageenan, gum Arabic (e.g. from acacia tree), isinglass, or isofluoroside; or polymers such as dextrans, levans, gelatin or polyethylene glycol. Polyethylene glycol, long gelatins, short gelatins, soluble starches, polyvinylpyrrolidone (PVP), long chain alcohols, alginates, tragacanth, bentonite, carbomer, and nanoparticles can also be useful to stabilize bubbles. Rheology modifiers can be useful for adjusting the flow properties of a foam. Examples include, but are not limited to, short carbohydrates, long carbohydrates, proteins, ionic surfactants non-ionic surfactants, water soluble fluorocarbon surfactants and salts.

A gas delivery component will typically be configured to deliver gas to a bubble generator component or flow cell under positive pressure. However, in some configurations, gas can be delivered under negative pressure. Inert gases such as $N_2$ or noble gases are particularly beneficial because they will have reduced risk of adversely interacting with biological components such as enzymes and nucleic acids. In some configurations, a system of the present disclosure, and in particular the gas delivery component, will be configured to prevent molecular oxygen from entering a fluid foam. For example, the system and its fluidic components can be configured to exclude atmospheric oxygen. As such the gas bubbles in a fluid foam can be substantially devoid of molecular oxygen. For example, the bubbles in a fluid foam can contain less than 20%, 10%, 1%, 0.5%, 0.1%, 100 ppm, 10 ppm or less of molecular oxygen. Alternatively, a system or gas delivery component can be configured to deliver molecular oxygen or atmospheric oxygen if desired for a particular application. In some configurations, the gas is atmospheric air, which can optionally be filtered prior to entering the liquid stream. Filtering can be used for air or other gases to remove particulates and other impurities.

Figure 6:
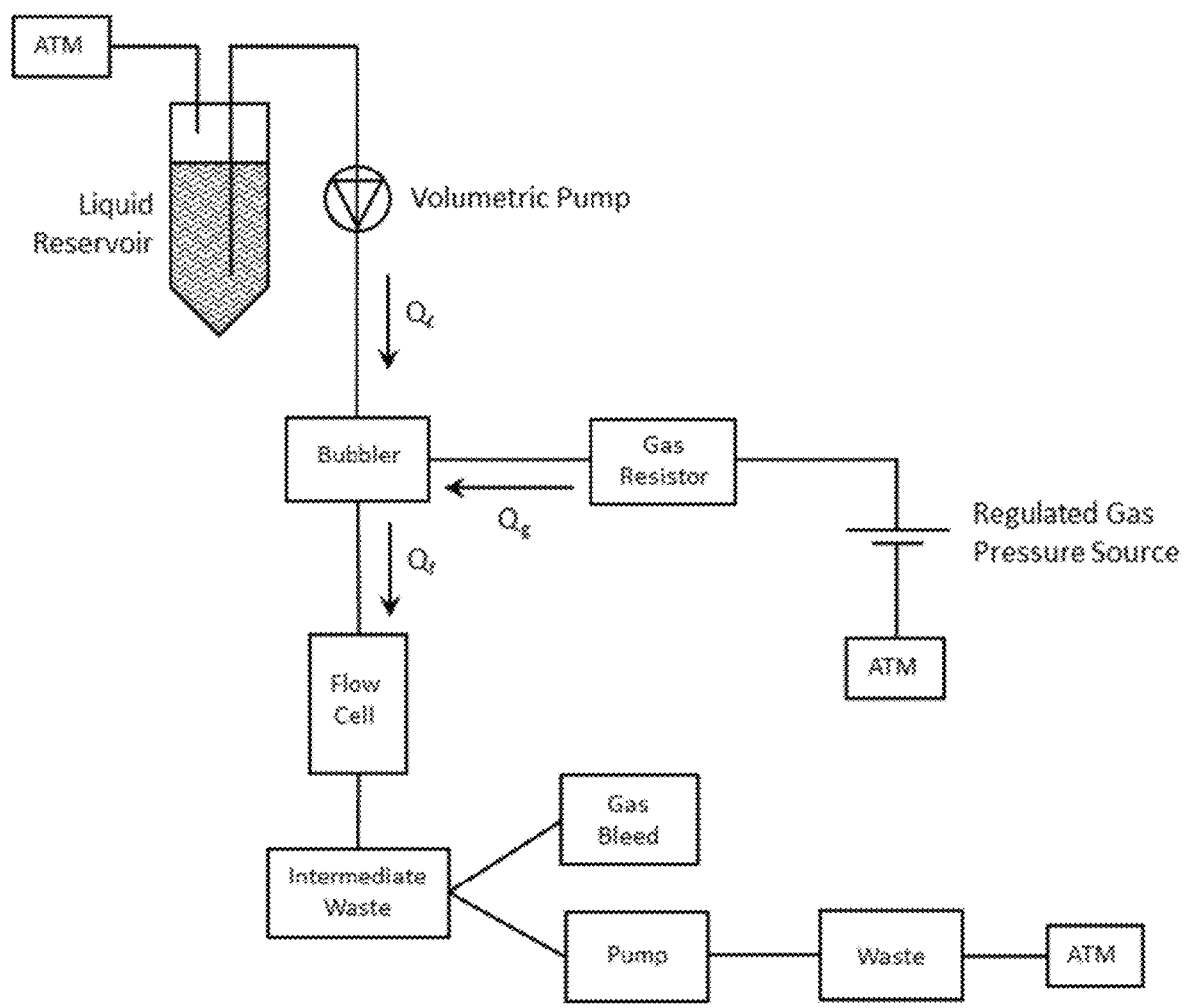
FIG. 6 shows a fluidic circuit for delivering a fluid foam to a flow cell.

An exemplary fluidic circuit that includes a bubble generator ("bubbler") for delivering a foam to a flow cell is shown in FIG. 6. A liquid reservoir contains a reagent or other liquid and is open to the atmosphere (ATM). The liquid can be delivered to a bubble generator under the force of a volumetric pump. Atmospheric air (ATM) is delivered to the bubble generator (Bubbler) under the force of a regulated gas pressure source. The fluidic circuit may include an optional gas resistor (shown in FIG. 6). In some configurations, a membrane that is within the bubble generator, or in the gas line upstream of the bubble generator, will serve as a gas resistor. As an alternative or addition to the use of a membrane, other types of gas resistors can be placed upstream in the gas line, examples of which include a microorifice (e.g. available from O'Keefe Controls Co., Monroe Conn.) or a capillary resistor. A fluid foam forms due to the mixing of gas and liquid in the bubble generator. The fluid foam flows to the flow cell and then to an intermediate waste reservoir. Gas can be vented from the intermediate waste reservoir and liquid can be moved to a downstream waste reservoir under the force of a pump. The downstream waste reservoir is open to atmosphere (ATM).

As shown in FIG. 6, the volumetric flow rate for the fluid foam ($Q_f$) can be adjusted by modifying the volumetric flow rate of the liquid ($Q_l$) and the volumetric flow rate of the gas ($Q_g$). The flow rates can be adjusted or evaluated using Poiseuille's equation for compressible fluids. For a compressible fluid in a tube the volumetric flow rate and the linear velocity are not constant along the tube. The flow is usually expressed at outlet pressure. As fluid is compressed or expands, work is done and the fluid is heated or cooled. This means that the flow rate depends on the heat transfer to and from the fluid. For an ideal gas in the isothermal case, where the temperature of the fluid is permitted to equilibrate with its surroundings, and when the pressure difference between ends of the tube is small, the volumetric flow rate at the tube outlet is given by Equation 2:

$$Q = \frac{dV}{dt} = v\pi R^2 = \frac{\pi R^4 (P_i - P_o)}{8 \mu L} \times \frac{P_i + P_o}{2 P_o} = \frac{\pi R^4}{16 \mu L}\left(\frac{P_i^2 - P_o^2}{P_o}\right)$$

wherein $P_i$ is inlet pressure, $P_o$ is outlet pressure, L is the length of the tube, $\mu$ is viscosity, R is radius of the tube, V is volume of the fluid at the outlet pressure and v is the velocity of the fluid at the outlet pressure.

A bubble bolus can be used for efficient exchange of different fluids in a system set forth herein. Taking the system of FIG. 6 as an example, the bubble generator ('bubbler') can be used to produce a bubble bolus to the common fluid line upstream of the flow cell. A fluid foam can be produced in the common fluid line by configuring the volumetric pump to move liquid from the reservoir to the flow cell while gas is delivered to the bubbler at a relatively high pressure. The combined effect of the pump and gas pressure produces the foam and moves it into the flow cell. A bubble bolus can be produced by reversing the direction of the pump and reducing the pressure of the gas being delivered to the bubbler. The combined effect is to draw the fluid foam from the common fluid line toward the reservoir and filling the common fluid line with a bubble bolus. The fluid foam in the flow cell will be retained since the gas pressure is reduced to a level that is lower than the back pressure on the flow cell. The direction of the volumetric pump can then be reversed, and the gas pressure can be returned to the relatively high pressure that was used to produce fluid foam. This action will direct the bubble bolus through the common fluid line, and the bolus will be chased by liquid from the reservoir. The bolus will pass through the bubbler and into the flow cell followed by the liquid which will become foam at the bubbler prior to entering the flow cell. In the present example, only a single liquid reservoir is described. It will be understood that multiple reservoirs can be used, and they can be connected to the common fluid line, for example, via a rotary valve. The rotary valve can be upstream of the volumetric pump such that the valve is cleared of fluid foam by the bubble bolus that was produced as set forth above.

A system of the present disclosure can optionally include an optical detection system configured to detect the inside of a flow cell such as the inside of a detection channel in a flow cell. Particularly useful optical detection systems include those that are found in sub-systems or components of nucleic acid sequencing systems. Several such detection apparatus are configured for optical detection, for example, detection of luminescence signals. Accordingly, an optical detection system can include an excitation system configured to irradiate the inside of a flow cell channel. The optical detection system can further include an emission system configured to detect luminescence from the inside of the flow cell channel. Detection of luminescence can be carried out using methods known in the art pertaining to nucleic acid arrays or nucleic acid sequencing. A luminophore can be detected based on any of a variety of luminescence properties including, for example, emission wavelength, excitation wavelength, fluorescence resonance energy transfer (FRET) intensity, quenching, anisotropy or lifetime.

Examples of detection apparatus and components thereof that can be used in a system or method herein are described, for example, in US Pat. App. Pub. No. 2010/0111768 A1 or U.S. Pat. No. 7,329,860; 8,951,781 or 9,193,996, each of which is incorporated herein by reference. Other detection apparatus include those commercialized for nucleic acid sequencing such as those provided by Illumina™, Inc. (e.g.

HiSeq™, MiSeq™, NextSeq™, or NovaSeq™ systems), Life Technologies™ (e.g. ABI PRISM™, or SOLID™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety.

Although the system and methods of the present disclosure are illustrated in the context of optical detection in several exemplary embodiments herein, it will be understood that other detection modalities can be used in addition or instead. For example, the detector can be an electronic detector used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.) or as used in detection of nanopores such as those commercialized by Oxford Nanopore™, Oxford UK (e.g. MinION™ or PromethION™ systems) or set forth in U.S. Pat. No. 7,001,792; Soni & Meller, *Clin. Chem.* 53, 1996-2001 (2007); Healy, *Nanomed.* 2, 459-481 (2007); or Cockroft, et al. *J. Am. Chem. Soc.* 130, 818-820 (2008), each of which is incorporated herein by reference. A FET detector can be used such as one or more of those described in U.S. Pat. App. Ser. No. 62/767,712; US Pat. App. Pub. Nos. 2017/0240962 A1, 2018/0051316 A1, 2018/0112265 A1, 2018/0155773 A1 or 2018/0305727 A1; or U.S. Pat. Nos. 9,164,053, 9,829,456, 10,036,064, or 10,125,391, each of which is incorporated herein by reference.

Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Mixed-phase fluids, such as foams, can be used for delivery or removal of reagents, analytes, products or the like from a flow cell that is to be examined in a method set forth herein. In some configurations, the mixed-phase fluid will be present in the flow cell during an examination or detection step. For example, the mixed-phase fluid can be flowing through the flow cell during the examination or detection step. Alternatively, mixed-phase fluid can be absent from a flow cell during a detection or examination step of a method set forth herein.

Control of system components, such as a bubble generator or phase mixing component, can utilize a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. For example, a processor or other device can be programmed to actuate a valve or other fluidic component that controls the flow of particles, gas or liquid, into a phase mixing component thereby creating a mixed-phase fluid having a desired number of bubbles or globules, bubbles or globules of a desired size or composition, or other desirable characteristics of bubbles or globules. As an alternative or addition to controlling the flow of the material that will form the dispersed phase of the mixed-phase fluid, a processor or other device can be programmed to actuate a valve or other fluidic component that controls the flow of the liquid that will form the bulk phase of the mixed-phase fluid. The same or different processor that is used to control fluids can interact with the system to acquire, store and process signals (e.g. signals detected in a method set forth herein). In particular embodiments, a processor can be used to determine, from the signals, the identity of the nucleotide that is present at a particular location in a template nucleic acid. In some cases, the processor will identify a sequence of nucleotides for the template from the signals that are detected.

A useful processor can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The processor can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The processor may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein such as controlling the concentration, number, size, polydispersity or composition of bubbles, globules or particles that are delivered to a liquid to create a mixed-phase fluid.

The components of a processor or other programmable device may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A processor can optionally communicate with one or more external devices such as a keyboard, a pointing device (e.g. a mouse), a display, such as a graphical user interface (GUI), or other device that facilitates interaction of a user with a system of the present disclosure. Similarly, the processor can communicate with other devices (e.g., via network card, modem, etc.). Such communication can occur via I/O interfaces. Still yet, a processor of a system herein may communicate with one or more networks such as a local area network (LAN), a general wide area network (WAN), and/or a public network (e.g., the Internet) via a suitable network adapter.

The present disclosure further provides a method for detecting an analyte of interest, the method including steps of (a) providing an analytical system including (i) a flow cell having an analyte of interest immobilized therein, (ii) a phase mixing component that mixes a liquid phase with a second phase at a predefined rate; (b) delivering a series of fluids to the inside of the flow cell to bind to the analyte or modify the analyte, wherein at least one of the fluids is a mixed-phase fluid produced by the phase mixing component to include bubbles, globules or particles of the second phase suspended in the liquid phase, thereby detecting the analyte of interest.

In a particular configuration, a method for sequencing a nucleic acid is provided, the method including steps of (a) providing a sequencing system including (i) a flow cell having a nucleic acid immobilized therein, (ii) a phase mixing component that mixes a liquid phase with a second phase at a predefined rate; (b) delivering a series of fluids to the inside of the flow cell to perform a cycle of a sequencing process, wherein at least one of the fluids is a mixed-phase fluid produced by the phase mixing component to include bubbles, globules or particles of the second phase suspended in the liquid phase; and (c) repeating step (b), thereby determining the sequence for the nucleic acid.

Particularly useful sequencing processes are cyclical processes that employ repeated cycles of reagent delivery. Each cycle can include one step or multiple steps. For example, each cycle can include all steps needed to detect a single nucleotide position in a template nucleic acid. Some sequencing processes employ cyclical reversible terminator (CRT) chemistry in which each cycle includes steps for (i) adding a single reversibly terminated nucleotide to increment a nascent primer to a nucleotide position that is to be detected; (ii) detecting the nucleotide at the single nucleotide position, and (iii) deblocking the nascent primer to allow a return to step (i) to start a subsequent cycle. One or more of these steps can be carried out in a mixed-phase fluid. In some configurations, all three steps are carried out in a mixed-phase fluid. A mixed-phase fluid can be used to deliver and/or remove reagents or products of one or more of these steps. Examples of reaction steps, reagents, and products that can be used in a CRT process that uses mixed-phase fluids are set forth below and in the references cited below. Alternatively, one or more of the exemplified steps, reagents or products can be carried out in the absence of a mixed-phase fluid.

A specific example of a useful CRT nucleic acid sequencing process is a Sequencing By Binding™ (SBB™) reaction, for example, as described in commonly owned US Pat. App. Pub. Nos. 2017/0022553 A1; 2018/0044727 A1; 2018/0187245 A1; or 2018/0208983 A1, each of which is incorporated herein by reference. Generally, SBB™ methods for determining the sequence of a template nucleic acid molecule can be based on formation of a stabilized ternary complex (between polymerase, primed nucleic acid and cognate nucleotide) under specified conditions. The method can include an examination phase followed by a nucleotide incorporation phase. One or more sequencing phases can be carried out using a mixed-phase fluid (e.g. a fluid foam, fluid slurry or fluid emulsion).

The examination phase of an SBB™ process can be carried out in a flow cell, the flow cell containing at least one template nucleic acid molecule primed with a primer by delivering to the flow cell reagents to form a first reaction mixture. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out by scanning the flow cell using an apparatus or method set forth herein.

During the examination phase of an SBB™ process, discrimination between correct and incorrect nucleotides can be facilitated by ternary complex stabilization. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include scanning of the flow cell using apparatus and methods set forth herein. One or more reagents used in an examination phase of an SBB™ reaction can optionally be delivered via a mixed-phase fluid (e.g. a fluid foam, fluid slurry or fluid emulsion) or contacted with a mixed-phase fluid. A mixed-phase fluid can be removed from a flow cell during an examination phase, for example, to facilitate detection.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added. It will be understood that any of a variety of nucleic acid sequencing reactions can be carried out using an apparatus and method of the present disclosure. Other exemplary sequencing methods are set forth below. One or more reagents used in an extension phase of an SBB™ reaction can optionally be delivered via a mixed-phase fluid (e.g. a fluid foam, fluid slurry or fluid emulsion), contacted with a mixed-phase fluid and/or removed by a mixed-phase fluid.

Washes can be carried out between the various delivery steps of an SBB™ process. Wash steps can be performed between any of a variety of steps set forth herein. For example, a wash step can be useful for separating a primed template nucleic acid from other reagents that were contacted with the primed template nucleic acid under ternary complex stabilizing conditions during an SBB™ process. Such a wash can remove one or more reagents from interfering with examination of a mixture or from contaminating a second mixture that is to be formed on a substrate (or in a vessel) that had previously been in contact with the first mixture. For example, a primed template nucleic acid can be contacted with a polymerase and at least one nucleotide type to form a first mixture under ternary complex stabilizing conditions, and the first mixture can be examined. Optionally, a wash can be carried out prior to examination to remove reagents that are not participating in formation of a stabilized ternary complex. Alternatively or additionally, a wash can be carried out after the examination step to remove one or more component of the first mixture from the primed template nucleic acid. Then the primed template nucleic acid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex. One or more of the washes can optionally employ a mixed-phase fluid (e.g. a fluid foam, fluid slurry or fluid emulsion).

Another useful CRT sequencing process is sequencing-by-synthesis (SBS). SBS generally involves the enzymatic extension of a nascent primer through the iterative addition of nucleotides against a template strand to which the primer is hybridized. Briefly, SBS can be initiated by contacting target nucleic acids, attached to sites in a flow cell, with one or more labeled nucleotides, DNA polymerase, etc. Those sites where a primer is extended using the target nucleic acid as template will incorporate a labeled nucleotide that can be detected. Detection can include scanning using an apparatus or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a method, system or apparatus of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.). One or more reagents used in an SBS process can optionally be delivered via a mixed-phase fluid (e.g. a fluid foam, fluid slurry or fluid emulsion), contacted with a mixed-phase fluid, and/or removed by a mixed-phase fluid. A mixed-phase fluid can be removed from a flow cell for detection during an SBS process.

Some SBS embodiments are cyclical but need not employ reversible terminator nucleotides. Such methods can also employ mixed-phase fluids. A particularly useful method includes detection of a proton released upon incorporation of a nucleotide into an extension product. For example, sequencing based on detection of released protons can use reagents and an electrical detector that are commercially available from Thermo Fisher (Waltham, Mass.) or described in US Pat. App. Pub. Nos. 2009/0026082 A1; 2009/0127589 A1; 2010/0137143 A1; or 2010/0282617 A1, each of which is incorporated herein by reference. One or more reagents used in an SBS process that employs proton detection can optionally be delivered via a mixed-phase fluid (e.g. a fluid foam, fluid slurry or fluid emulsion) or contacted with a mixed-phase fluid. Mixed-phase fluids can be particularly useful for removing reagents, for example, during a wash step.

Other cyclical sequencing processes can be used, such as pyrosequencing. Pyrosequencing detects the release of inorganic pyrophosphate (PPi) as nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. One or more reagents used in a pyrosequencing process can optionally be delivered via a mixed-phase fluid (e.g. a fluid foam, fluid slurry or fluid emulsion) or contacted with a mixed-phase fluid. Mixed-phase fluids can be particularly useful for removing reagents, for example, during a wash step.

Sequencing-by-ligation reactions are also useful including, for example, those described in Shendure et al. *Science* 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using a system or method set forth herein. One or more reagents used in a sequencing-by-ligation process can optionally be delivered via a mixed-phase fluid (e.g. a fluid foam, fluid slurry or fluid emulsion) or contacted with a mixed-phase fluid. Mixed-phase fluids can be particularly useful for removing reagents, for example, during a wash step.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 10, 25, 50, 100, 150, 250, 500 or more cycles. Alternatively or additionally, no more than 500, 250, 150, 100, 50, 25, 10, 2 or 1 cycles are carried out.

Some embodiments can utilize methods involving real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zero-mode waveguides (ZMW). Techniques and reagents for sequencing via FRET and or ZMW detection that can be modified for use in an apparatus or method set forth herein are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008); or U.S. Pat. Nos. 7,315,019; 8,252,911 or 8,530,164, the disclosures of which are incorporated herein by reference. In real-time methods it can be beneficial to replace or modify reagent solutions periodically. Replacement or modification can optionally employ a mixed-phase fluid (e.g. a fluid foam, fluid slurry or fluid emulsion).

Although the methods, compositions and apparatus of the present disclosure have been exemplified in the context of nucleic acid sequencing procedures, other procedures can benefit as well. The methods, compositions and apparatus are particularly useful for procedures that include repetitive steps such as reactions for synthesizing polymers in which cycles of monomer addition are repeated. A particularly relevant synthetic process is synthesis of nucleic acids. In some configurations, nucleoside phosphoramidites are the monomers that are repetitively added to a growing nucleic acid monomer. Nucleoside phosphoramidites include derivatives of natural or synthetic nucleosides in which protection groups (sometimes referred to a blocking groups) are added to reactive exocyclic amine and hydroxy groups, and in which an N,N-diisopropyl phosphoramidite group is attached to the 3'-hydroxy group of each nucleoside. Examples of protecting groups include, but are not limited to, acid-labile dimethoxytrityl (DMT) groups.

In some configurations, nucleic acids can be synthesized by covalently attaching a first nucleoside with DMT group to a solid support. The nucleoside can be attached to a solid support through a linker as described further herein. Nucleic acids can be synthesized through repeated cycles of deprotection and coupling. Nucleoside phosphoramidites, deprotection agents and other reagents used for synthesis of a growing nucleic acid, such as those set forth in further detail below, can be moved to and from a flow cell or other vessel using mixed-phase fluids.

In some embodiments described herein, a cycle of nucleic acid synthesis can include four steps. In particular, a typical nucleic acid synthesis cycle includes a deblocking step, a coupling step, a capping step, and an oxidation step. In the deblocking step, the DMT group of the attached nucleoside is removed with an acidic solution, for example, dichloroacetic acid or trichloroacetic acid in dichloromethane. In the coupling step, the phosphoramidite group of a nucleoside is activated by protonation using reagents such as an acidic azole catalyst, for example, tetrazole, 2-ethylthiotetrazole, 2-bezylthiotetrazole or 4,5-dicyanoimidazole. The mixture is brought into contact with the attached deblocked nucleoside or attached deblocked oligonucleotide of subsequent cycles. The activated phosphoramidite group reacts with the 5'-hydroxy group of the attached nucleoside. This reaction is sensitive to moisture and can be performed under anhydrous conditions, for example, using anhydrous acetonitrile. In the capping step, unreacted bound 5'-hydroxyoligonucleotides are quenched, for example by acetylation, or by providing the reactive hydroxyls with an electron deficient reaction center, in order to prevent the formation of side products during subsequent synthesis cycles. Reagents such as acetic anhydride and 1-methylimidazole can be used. In the oxidation step, the newly formed tricoordinated phosphite triester linkage can be treated with reagents such as iodine and water in the presence of a weak base, such as pyridine, lutidine, or collidine. Subsequent cycles typically begin with a deblocking step.

The process of synthesizing a nucleic acid can be carried out with a desired sequence of nucleotide additions and repeated until the oligonucleotides reach a desired sequence composition and length. At this point, the DMT group can be removed from the most 5' nucleoside residue and the nucleic acid can be cleaved from the solid support using agents such as aqueous ammonium hydroxide, aqueous methylamine, gaseous ammonia or gaseous methylamine. One or more of steps of a nucleic acid synthesis process, such as the steps set forth herein, can employ a mixed-phase fluid for delivery of reagents, removal of reagents or washing of a substrate upon which synthesis occurs.

Additional configurations of the methods, compositions and apparatus described herein relate to the synthesis of other polymeric molecules. For example, compositions, methods, and apparatus described herein can be configured to synthesize polypeptides. The process of peptide synthesis on solid supports can involve building a peptide from the carboxyl-terminal end. The peptide can be attached to a solid support via its carboxy-terminal amino acid. The peptide can include a protecting group on the amino-terminal alpha amino moiety. The protecting group can then be cleaved off the peptide to form a deprotected peptide. Next, a monomeric amino acid, also containing an alpha amino protecting group, can be contacted with the de-protected peptide under conditions for formation of a peptide bond between the alpha amino moiety of the deprotected peptide and the alpha carboxy moiety of the monomeric amino acid. The monomeric amino acid can be provided in an activated form or an activating reagent can be added to the amino acid and growing peptide. Washes can be carried out between steps to remove reagents. The cycle of deprotecting the prior amino acid and coupling the additional amino acid can be repeated until a peptide of the desired length is synthesized. Any reactive side chains of the amino acids are typically protected by chemical groups that can withstand the coupling and deprotection procedure. These side chain protecting groups, however, can be removed at the end of the synthesis. Useful reaction schemes for peptide synthesis include, for example, those described in Goodman et al. (Eds.). *Synthesis of Peptides and Peptidomimetics*, Vol. E22a. Georg Thieme Verlag, Stuttgart (2002), which is incorporated herein by reference. One or more of steps of a peptide synthesis process, such as the steps set forth herein, can employ a mixed-phase fluid for delivery of reagents, removal of reagents or washing of a substrate upon which synthesis occurs.

One or more of the steps set forth above for nucleic acid synthesis or peptide synthesis can be carried out in a mixed-phase fluid. In some configurations, all of the steps of the respective method are carried out in a mixed-phase fluid. A mixed-phase fluid can be used to deliver and/or remove reagents or products of one or more of these steps. Alternatively, one or more of the exemplified steps, reagents or products of a nucleic acid or peptide synthesis method can be carried out in the absence of a mixed-phase fluid.

Example 1

Nucleic Acid Sequencing with and without Bubbles

This example provides a comparison of nucleic acid sequencing using a liquid to deliver reagents or a fluid foam to deliver the reagents. The comparison demonstrated that a fluid foam can be used instead of a liquid in order to deliver sequencing reagents to an array of nucleic acids during a sequencing run. The results also showed that using a fluid foam in place of a liquid delivery medium provided substantial reduction in the consumption of reagents resulting in lower reagent costs and reduction of waste volumes. The quality of sequencing data obtained using fluid foam to deliver sequencing reagents was comparable to the quality of results obtained using a liquid to deliver the reagents.
Materials and Methods Flow cells containing primed template nucleic acids were prepared using liquid reagents as follows. Template nucleic acid strands synthesized in 12 PCR reactions were prepared, and then independently bound to beads. This resulted in a population of 12 bead types, where each bead harbored a homogenous collection of one of the 12 template strands. Beads harboring immobilized template strands were next attached to the inner surface of a flow cell. The inner surface of the flow cell was hydrophilized to inhibit bubbles from adhering to the flow cell surface. Next, sequencing primers were flowed into the flow cell and allowed to hybridize to the immobilized template strands to form immobilized primer-template hybrids.

Sequencing was performed cyclically, where each cycle included steps for (i) extension: adding a reversibly terminated nucleotide to the primers of the immobilized primer-template hybrids, (ii) examination: forming and detecting stabilized ternary complexes on the reversibly terminated, immobilized primer-template hybrids, and (iii) activation: cleaving the reversible terminator from the extended primers. Each cycle resulted in addition of a single nucleotide and detection of a subsequent nucleotide position. As such the number of cycles correlated directly with the length of the sequence read for each bead. Table 1 shows the steps carried out for each individual cycle of a control sequencing run that was performed in liquid phase (i.e. absent introduced bubbles) along with the time for each step, flow rate for the fluidic reagents and total volume of liquid reagent consumed in each step.

TABLE 1

Sequencing Cycle for Liquid Phase Sequencing (No Bubbles)

| STEP | TIME (SEC) | LIQUID PHASE FLOW RATE (µL/SEC) | LIQUID PHASE TOTAL VOLUME CONSUMED (µL) |
|---|---|---|---|
| RTS | 5 | 32 | 160 |
| RTS | 30 | 1 | 30 |
| NSB | 5 | 32 | 160 |
| EXT | 5 | 32 | 160 |
| PAUSE | 15 | 0 | 0 |
| IMG | 7 | 32 | 224 |
| DETECT | 1 | 0 | 0 |
| NSB | 5 | 32 | 160 |
| EXA | 5 | 32 | 160 |
| PAUSE | 15 | 0 | 0 |
| IMG | 7 | 32 | 224 |
| DETECT | 1 | 0 | 0 |
| NSB | 5 | 32 | 160 |
| EXC | 5 | 32 | 160 |
| PAUSE | 15 | 0 | 0 |
| IMG | 7 | 32 | 224 |
| DETECT | 1 | 0 | 0 |
| NSB | 5 | 32 | 160 |
| EXG | 5 | 32 | 160 |
| PAUSE | 15 | 0 | 0 |
| IMG | 7 | 32 | 224 |
| DETECT | 1 | 0 | 0 |
| NSB | 5 | 32 | 160 |
| CLV | 5 | 32 | 160 |
| CLV | 12 | 1 | 12 |
| IMG | 5 | 32 | 160 |

The sequencing cycle was initiated by incorporating reversible terminator nucleotides at the 3'-ends of the primers of the immobilized primer-template hybrids. This was accomplished by the RTS step in which the flow cell was contacted with unlabeled reversibly terminated nucleotide analogs of dATP, dGTP, dCTP, and dTTP) in the presence of M15 polymerase (see U.S. Pat App. Ser. No. 62/732,510, which is incorporated herein by reference). The reversible terminator nucleotide used in this illustrative procedure included a 3'-$ONH_2$ reversible terminator moiety. A description of this reversible terminator nucleotide can be found in U.S. Pat. No. 7,544,794, which is incorporated herein by reference.

The NSB step was carried out to remove the dNTPs from the RTS solution and to wash the flow cell. More specifically, for the NSB step a solution containing isopropanol, Tween-80, hydroxylamine and EDTA was flowed through the flow cell. The NSB step retained the M15 polymerase (see U.S. Pat. No. 10,400,272, which is incorporated herein by reference.

The cycle then continued with an examination subroutine in which each of four different nucleotides was individually delivered to the flow cell (EXT, EXA, EXC and EXG, delivered Cy5 labeled dTTP, Cy5 labelled dATP, Cy5 labeled dCTP and Cy5 labeled dGTP, respectively), the system paused fluid flow to allow formation of ternary complex, the free nucleotide was removed from the flow cell by delivery of IMG reagent and then the flow cell was examined for ternary complex formation at the immobilized primer-template hybrids. The IMG reagent included LiCl, betaine, Tween-80, KCl, Ammonium Sulfate, hydroxylamine, and EDTA which stabilized the ternary complexes after removal of free nucleotides (see U.S. patent application Ser. No. 16/355,361, which is incorporated herein by reference). The flow cell was imaged via fluorescence microscopy to detect ternary complexes that contained a labeled nucleotide that was a cognate for the next correct nucleotide in each of the template nucleic acids. Reversible terminator moieties on the 3' nucleotides of the primer strands precluded nucleotide incorporation during the ternary complex formation and detection steps.

Following the examination subroutine, the NSB wash was carried out to clear the flow cell of the nucleotides from the examination subroutine. Then the sequencing cycle continued with the CLV step in which the reversible terminator moieties were removed from the primers using sodium acetate and sodium nitrite as set forth in U.S. Pat. No. 7,544,794, which is incorporated herein by reference. The flow cell was then washed in IMG solution. Polymerase from the examination steps was removed by the CLV and IMG steps. The sequencing process then proceeded to the next nucleotide position by returning to the first step of the next cycle.

Table 2 shows the steps carried out for each individual cycle of a sequencing run that was performed in fluid foam. The table shows the duration, liquid reagent flow rate, liquid volume consumption and gas pressure used for each step. The liquid phase of each step was the same as those of the same name in the control sequencing run as set forth above in the context of Table 1. However, the liquid phase was mixed with gas for several of the steps using a bubble generator having a Y junction and gas diffuser as shown in FIG. 5. The bubble generator was placed downstream of reservoirs that contained the liquid reagents and upstream of the flow cell. The bubble generator created a foam when the pressure was above 2 PSI (pounds per square inch). For detection steps the gas pressure was reduced to 2 PSI to omit bubbles. Accordingly, detection was carried out absent foam in a liquid reagent as done in the control sequencing run of Table 1.

TABLE 2

Sequencing Cycle for Fluid Foam Sequencing (+Bubbles)

| STEP | TIME (SEC) | LIQUID PHASE FLOW RATE (µL/SEC) | LIQUID PHASE TOTAL VOLUME CONSUMED (µL) | GAS PHASE PRESSURE (PSI) |
|---|---|---|---|---|
| RTS | 5 | 10 | 50 | 15 |
| RTS WIGGLE | 30 | 0 | 0 | 2 |
| NSB | 5 | 10 | 50 | 10 |
| NSB WIGGLE | 5 | 0 | 0 | 2 |
| EXT | 5 | 10 | 50 | 20 |
| EXT | 1.5 | −10 | 0 | 2 |
| PAUSE | 15 | 0 | 0 | 2 |
| IMG | 5 | 10 | 50 | 15 |
| IMG | 1 | 50 | 50 | 2 |
| IMG | 1.5 | −10 | 0 | 2 |
| DETECT | 1 | 0 | 0 | 2 |
| NSB | 5 | 10 | 50 | 10 |
| NSB WIGGLE | 5 | 0 | 0 | 2 |
| EXA | 5 | 10 | 50 | 20 |
| EXA | 1.5 | −10 | 0 | 2 |
| PAUSE | 15 | 0 | 0 | 2 |
| IMG | 5 | 10 | 50 | 15 |
| IMG | 1 | 50 | 50 | 2 |
| IMG | 1.5 | −10 | 0 | 2 |
| DETECT | 1 | 0 | 0 | 2 |
| NSB | 5 | 10 | 50 | 10 |
| NSB WIGGLE | 5 | 0 | 0 | 2 |
| EXC | 5 | 10 | 50 | 20 |
| EXC | 1.5 | −10 | 0 | 2 |
| PAUSE | 15 | 0 | 0 | 2 |
| IMG | 5 | 10 | 50 | 15 |
| IMG | 1 | 50 | 50 | 2 |
| IMG | 1.5 | −10 | 0 | 2 |
| DETECT | 1 | 0 | 0 | 2 |
| NSB | 5 | 10 | 50 | 10 |
| NSB WIGGLE | 5 | 0 | 0 | 2 |
| EXG | 5 | 10 | 50 | 20 |
| EXG | 1.5 | −10 | 0 | 2 |
| PAUSE | 15 | 0 | 0 | 2 |
| IMG | 5 | 10 | 50 | 15 |
| IMG | 1 | 50 | 50 | 2 |
| IMG | 1.5 | −10 | 0 | 2 |
| DETECT | 1 | 0 | 0 | 2 |
| NSB | 5 | 10 | 50 | 10 |
| NSB WIGGLE | 5 | 0 | 0 | 2 |
| CLV | 3 | 10 | 30 | 15 |
| CLV | 2 | 10 | 20 | 2 |
| CLV | 12 | 1 | 12 | 2 |
| IMG | 5 | 10 | 50 | 15 |

Several steps set forth in Table 2 included a "wiggle" in which the direction of flow for the fluid foam was toggled back and forth to allow mixing in the flow cell. Several steps also included a sustained reverse of the flow direction for the fluid foam or liquid reagent. Reverse flow is indicated by negative values in the flow rate column and zero values for the total volume of fluid that passes through the flow cell.

Results

Figure 7:
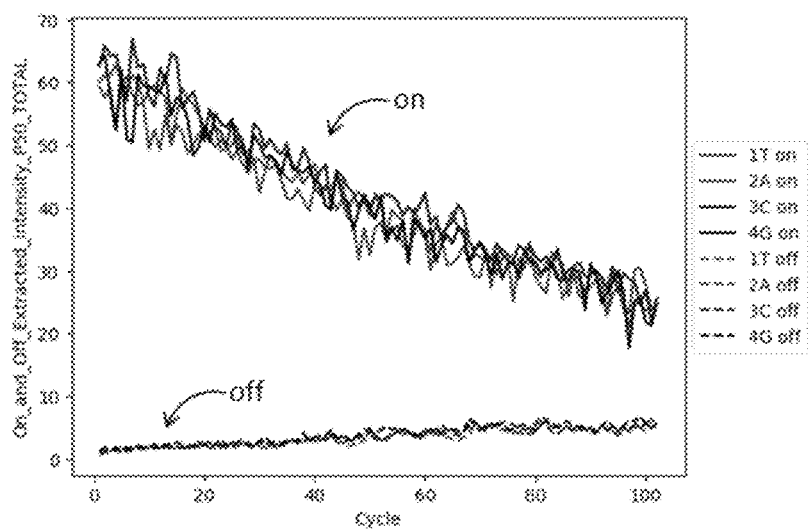
FIG. 7 shows plots of signal intensity vs. sequencing cycle for sequencing runs that used liquid delivery of reagents (FIG. 7A) or fluid foam delivery of the reagents (FIG. 7B).
Figure 7:
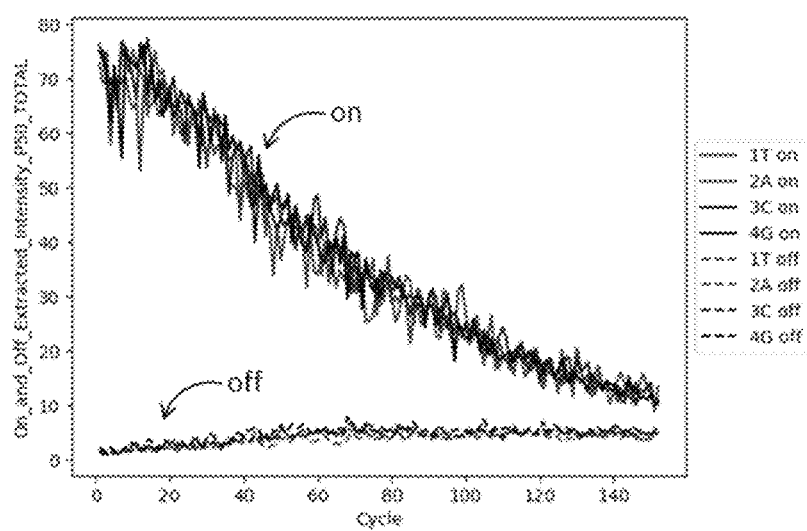

FIG. 7 shows plots of signal intensity vs. sequencing cycle for the sequencing protocol that used liquid delivery of reagents (FIG. 7A) or fluid foam delivery of reagents (FIG. 7B). Individual traces are shown for the 'on' intensity detected for each nucleotide type and for the 'off' intensity for each nucleotide type. For each bead in each cycle, the nucleotide type that produced the highest signal was identified as the 'on' signal and the other three nucleotide types were identified as the 'off' signal. The 'on' signals for each nucleotide type were averaged across all bead types detected in a given cycle, and the median intensity was plotted across all cycles (100 cycles were run using liquid delivery of reagents (FIG. 7A) and 150 cycles were run using fluid foam delivery of reagents (FIG. 7B)) to obtain each of the 'on' signal traces shown in the figure. Similar averaging of signal intensities across all bead types on a per cycle basis was used to arrive at the 'off' intensity traces shown in FIG. 7.

Signal decay for the 'on' traces was evaluated by fitting the traces to a curve defined by the following equation:

$$I = I_0 e^{-(n/\tau)} \qquad \text{(Equation 3)}$$

wherein I is signal intensity, n is the number of cycles and τ is the cycle when the signal is about 37% of $I_0$ (initial signal intensity). Higher τ is indicative of reduced rate of signal decay, which is generally preferred since it indicates increased read length and sequencing accuracy, whereas increased rate of signal decay is characterized by lower values for τ. The goodness of fit was calculated as the coefficient of determination, $R^2$. Higher $R^2$ values correlate with reduced signal intensity variance over the sequencing run. The traces for liquid delivery of reagents shown in FIG. 7A had an average τ of 83 and an average $R^2$ of 0.97; and the traces for fluid foam delivery of reagents shown in FIG. 7B had an average τ of 66 and an average $R^2$ of 0.97 (the averages were taken across the on traces for all four nucleotide types). As indicated by the τ values, although the use of fluid foam delivery of reagents in place of liquid reagent delivery produced a minor impact on read length, the use of fluid foam still allowed for relatively long read lengths. Moreover, the $R^2$ values were comparable for sequencing runs conducted with and without bubbles indicating that the use of fluid foam for delivering sequencing reagents had an insignificant impact on variance of signal intensity.

Table 3 shows post processing results for the sequencing run using liquid delivery of reagents as plotted in FIG. 7A. Table 4 shows sequencing results for the sequencing run using liquid delivery as plotted in FIG. 7B. The first column of each table shows the percent of the observed beads that are omitted from the analysis, where "PNN" includes all of the observed beads, P01 omits the lowest quality 1% of the data, P02 omits the lowest quality 2% of the data, etc. up to P06 which omits the lowest quality 6% of the data. For each row the number of "No Calls", "Right Calls" and "Wrong Calls" are shown along with the sum of those three columns shown under the "Total Calls" column. The percent of errors is shown along with the relevant Q score that was calculated for each value in the Q % column.

In nucleic acid sequencing applications, the Q score is a property that is logarithmically related to the base calling error probabilities (P) according to the following equation $$Q = -10 \log(P) \quad \text{(Equation 4)}$$

For example, a Q score of 20 (Q20) for a particular base call is equivalent to a 1 in 100 probability that the base call is incorrect. This means that the base call accuracy (i.e., the probability of a correct base call) is 99.0%. A higher base call accuracy of 99.9% is indicated by a Q score of Q30 and indicates an incorrect base call probability of 1 in 1000. Q40 indicates a base call accuracy of 99.99% (i.e. incorrect base call probability of 1 in 10,000), Q50 indicates an even higher base call accuracy of 99.999% (i.e. incorrect base call probability of 1 in 100,000), etc. Currently available high throughput sequencing platforms (i.e. 'next generation" sequencing platforms such as those available from Illumina, Inc., San Diego Calif.) typically use Q30 as a benchmark for quality. Higher Q scores are indicative of increased accuracy of variant calls, which provides increased accuracy of conclusions and reduced costs for validation experiments.

As indicated by the results of Table 3, when sequencing was carried out using liquid reagents a Q score of nearly Q50 was obtained without discarding any of the observed data. Omitting the lowest quality 1% of the data from the analysis yielded a Q score of Q70 (i.e. incorrect base call probability of 1 in 10,000,000). By comparison, delivery of the reagents in foam fluid instead of liquid produced a Q score of about 38 without discarding any data. A score of Q70 was obtained by omitting a mere 6% of the data. Accordingly, the use of foam fluid to deliver sequencing reagents resulted in highly accurate sequencing.

TABLE 3

Sequencing Results (No Bubbles)

| Q % | NO CALLS | RIGHT CALLS | WRONG CALLS | TOTAL CALLS | ERROR PERCENT | Q SCORE |
|---|---|---|---|---|---|---|
| PNN | 25 | 789688 | 8 | 789696 | 0.001 | 49.94 |
| P00 | 0 | 789688 | 8 | 789696 | 0.001 | 49.94 |
| P01 | 0 | 781846 | 0 | 781846 | 0 | 70 |
| P02 | 0 | 774056 | 0 | 774056 | 0 | 70 |
| P03 | 0 | 767193 | 0 | 767193 | 0 | 70 |
| P04 | 0 | 767193 | 0 | 767193 | 0 | 70 |
| P05 | 0 | 756686 | 0 | 756686 | 0 | 70 |
| P06 | 0 | 756686 | 0 | 756686 | 0 | 70 |

TABLE 4

Sequencing Results (with bubbles)

| Q % | NO CALLS | RIGHT CALLS | WRONG CALLS | TOTAL CALLS | ERROR PERCENT | Q SCORE |
|---|---|---|---|---|---|---|
| PNN | 966 | 1029434 | 160 | 1029594 | 0.016 | 38.09 |
| P00 | 0 | 1029434 | 160 | 1029594 | 0.016 | 38.09 |
| P01 | 0 | 1019277 | 21 | 1019298 | 0.002 | 46.86 |
| P02 | 0 | 1008994 | 8 | 1009002 | 0.001 | 51.01 |
| P03 | 0 | 998703 | 3 | 998706 | 0 | 55.22 |
| P04 | 0 | 988407 | 3 | 988410 | 0 | 55.18 |
| P05 | 0 | 978112 | 2 | 978114 | 0 | 56.89 |
| P06 | 0 | 967818 | 0 | 967818 | 0 | 70 |

Table 5 shows consumption of liquid reagents per step and sequencing cycle. The foam fluid was produced by adding bubbles to the liquid reagent. As such, the bubbles occupy volume in the fluid foam which effectively reduces the total amount of reagent in a given volume of fluid foam compared to the same volume of the liquid reagent. However, the concentration of reagent in the liquid phase of the fluid foam is the same as the apparent concentration of the reagent in the liquid reagent as experienced by nucleic acids on the surface of the flow cell. Thus, the nucleic acids on the surface are contacted with sequencing reagents that are at the same "apparent" concentration in the fluid foam as in the non-bubbled liquid reagent even though the total amount of reagent consumed per sequencing cycle is reduced when bubbles are added to make the fluid foam.

TABLE 5

Reagent Consumption Per Step Per Cycle

| REAGENT | +BUBBLES LIQUID CONSUMED | NO BUBBLES LIQUID CONSUMED | REAGENT SAVINGS |
|---|---|---|---|
| RTS | 50 | 190 | 74% |
| NSB | 250 | 800 | 69% |
| EXT | 50 | 160 | 69% |
| EXA | 50 | 160 | 69% |
| EXC | 50 | 160 | 69% |
| EXG | 50 | 160 | 69% |
| IMG | 500 | 1056 | 53% |
| CLV | 62 | 172 | 64% |
| TOTAL | 1062 | 2858 | 63% |

The results of Table 5 show that reagent savings between 53% and 74% were achieved by adding bubbles to the sequencing reagents. The overall reagent savings for each cycle was 63%. Nevertheless, as indicated by the results of FIG. 7 and Tables 3 and 4, the use of fluid foam for sequencing yielded read lengths and read qualities comparable to those produced using liquid phase reagents in the sequencing platform.

Example 2

Nucleic Acid Sequencing System that Utilizes Fluid Foam

This example describes a nucleic acid sequencing system that includes a stage, a liquid delivery component, a gas delivery component, a bubble generator component, and an optical detection component, wherein the stage is configured to accept a flow cell having a detection channel, wherein the optical detection component is configured to detect the interior of the detection channel, wherein the liquid delivery component is configured to deliver liquid from a plurality of reservoirs to the detection channel, wherein the gas delivery component is configured to deliver gas from one or more source to the bubble generator component, and wherein the bubble generator component is configured to introduce bubbles from the gas delivery component into liquid from the liquid delivery component at a location that is downstream of the plurality of reservoirs and upstream of the flow cell, thereby delivering to the detection channel a fluid foam that includes bubbles of the gas from the gas delivery component.

Several of the components and functions of the nucleic acid sequencing system are set forth in further detail below. It will be understood that the system is exemplary. One or more of the components set forth below can be omitted or replaced with other components, for example, as set forth elsewhere herein. Other components that are set forth herein can be added to the exemplary system without necessarily replacing a component exemplified below.

Figure 8:
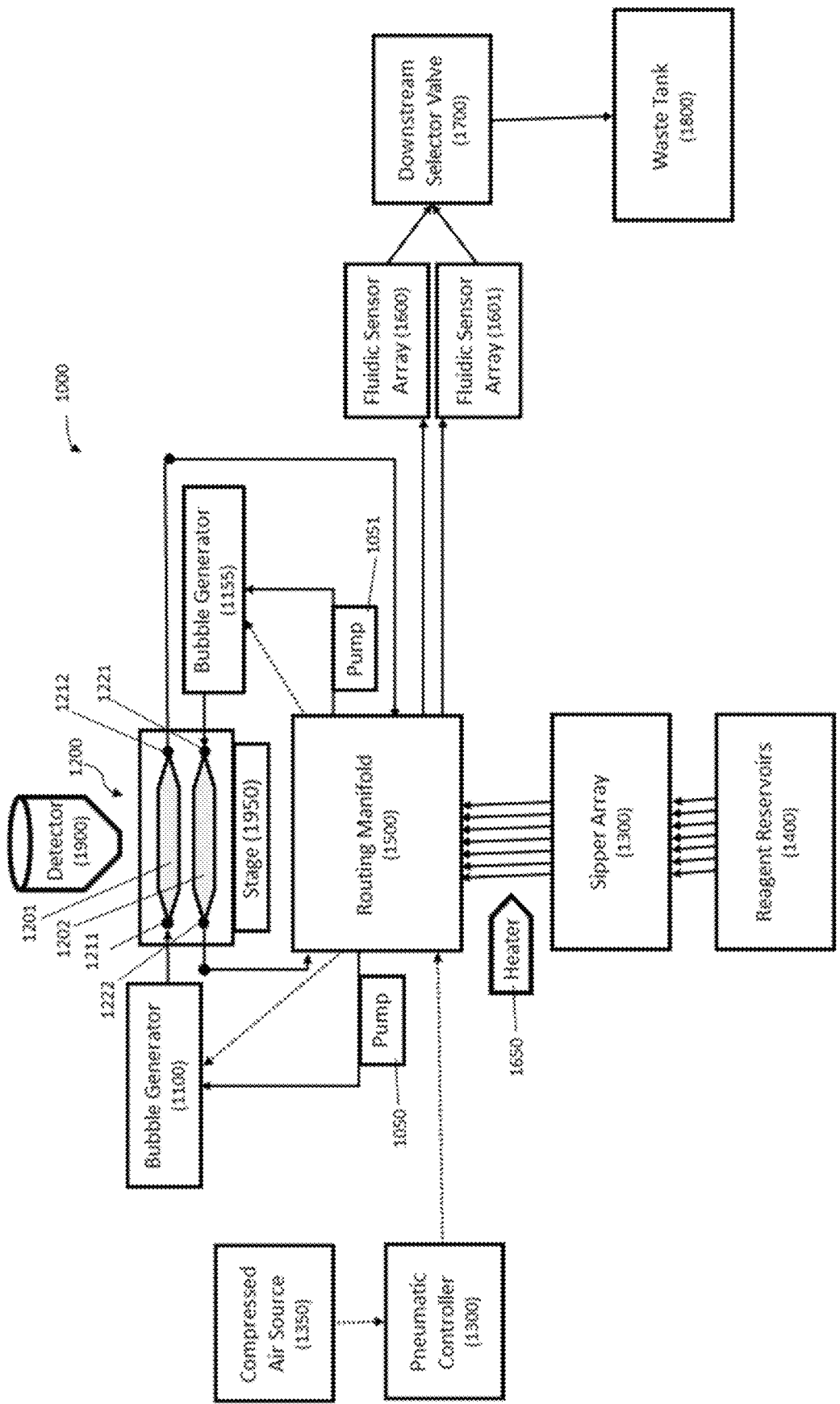
FIG. 8 shows a diagrammatic representation of functional components of a nucleic acid sequencing system.

A block diagram of nucleic acid sequencing system 1000 is shown in FIG. 8. Fluidic connections and the directions in which the fluids typically flow in system 1000 are indicated by arrows, wherein solid arrows indicate the flow of liquid or foam and dotted arrows indicate the flow of gas. In some circumstances, fluids can move in opposite directions, for example, when wiggling the fluids. The block diagram shows fluidic connections but is not intended to necessarily reflect the physical locations of the components, the lengths of the fluidic lines or the physical structure of the components.

Nucleic acid sequencing system 1000 includes sipper array 1300 which contacts liquids in the plurality of reagent reservoirs 1400. Sipper array 1300 is fluidically connected to routing manifold 1500 which directs liquid from individual sippers of sipper array 1300 to bubble generator 1100 or bubble generator 1155 (the bubble generators are also referred to as bubble generating components). Bubble generators 1100 and 1155 mix gas with the liquid to form a foam. Bubble generator 1100 is fluidically connected to ingress 1211 of detection channel 1201 of flow cell 1200. Bubble generator 1155 is fluidically connected to ingress 1221 of detection channel 1202 of flow cell 1200. The gas is directed to bubble generators 1100 and 1155 through a gas delivery component that includes compressed air source 1350 which directs gas through pneumatic controller 1300, through dedicated line in routing manifold 1500 to the bubble generators. The foam produced by bubble generator 1100 is directed to detection channel 1201 due to displacement forces applied to the liquid by pump 1050 or 1051 at a location in the liquid delivery component that is between the plurality of reagent reservoirs 1400 and the bubble generators 1100 and 1155. Egress 1212 for detection channel 1201 and egress 1222 are fluidically connected to routing manifold 1500 such that foam from detection channels 1201 and 1202, respectively, can be transferred downstream through fluidic sensor array 1600 or 1601 then through downstream selector valve 1700 to waste tank 1800. The downstream selector valve 1700 allows the fluidic systems passing through detection channel 1201 and detection channel 1202, respectively, to be selectively opened or closed.

Nucleic acid sequencing system 1000 further includes detector 1900. In this example, detector 1900 is an optical detector that includes an excitation system configured to irradiate the detection channels inside of flow cell 1200, and an emission system configured to detect luminescence from the detection channels inside the flow cell. Flow cell 1200 is positioned relative to the fluidic components and relative to detector 1900 by stage 1950. Nucleic acid sequencing system 1000 further includes heater 1650 which is configured to heat the liquids in the liquid delivery component at a location between plurality of reagent reservoirs 1400 and bubble generating component 1100.

Figure 9:
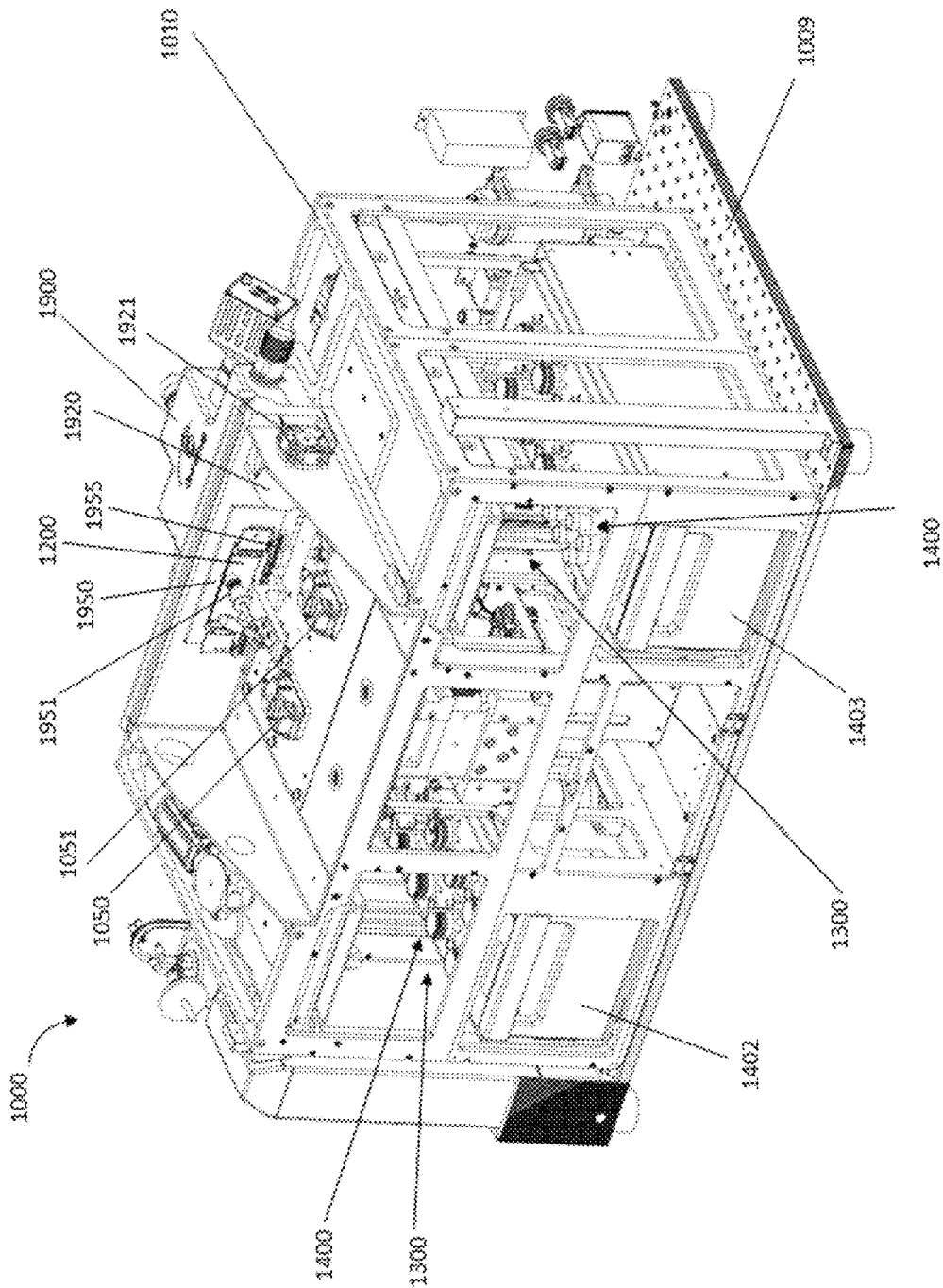
FIG. 9 shows a perspective view of an assembly of several components of a nucleic acid sequencing system.

FIG. 9 shows a perspective view of an assembly of several components of nucleic acid sequencing system 1000. System 1000 is supported by base 1009 and frame 1010. The top middle region of frame 1010 is configured for a user to access the system in order to place flow cell 1200 on stage 1950. Flow cell 1200 is pressed to stage 1950 by preload 1951. As such, flow cell 1200 is positioned to be detected by optical detector 1900. Flow cell 1200 is translated along stage 1950 by translational components 1955 and held to a reference surface on stage 1950 to allow detection of an array of nucleic acids (or other analytical sample) inside flow cell 1200. Components and operation of preload 1951, scanning system 1955 and optical detector 1900 are set forth in US Pat. App. Pub. No. 2019/0055596 A1, which is incorporated herein by reference. The system also includes vent pipe 1920 and fan 1921 for removing heat generated by the optical detector.

As shown in FIGS. 8 and 9, nucleic acid sequencing system 1000 further includes peristaltic pumps 1050 and 1051 which are configured to apply liquid displacement forces (e.g. positive pressure, positive displacement or the like) at a location in the liquid delivery component that is between plurality of reservoirs 1400 and bubble generators 1100 and 1155, thereby delivering liquid from the liquid delivery component to flow cell 1200. In exemplary system 1000, the pumps can be configured to apply liquid displacement forces to the liquid delivery component at a location that is between the rotary valve and the bubble generator component, thereby delivering liquid from the liquid delivery component to the flow cell.

Figure 12A:
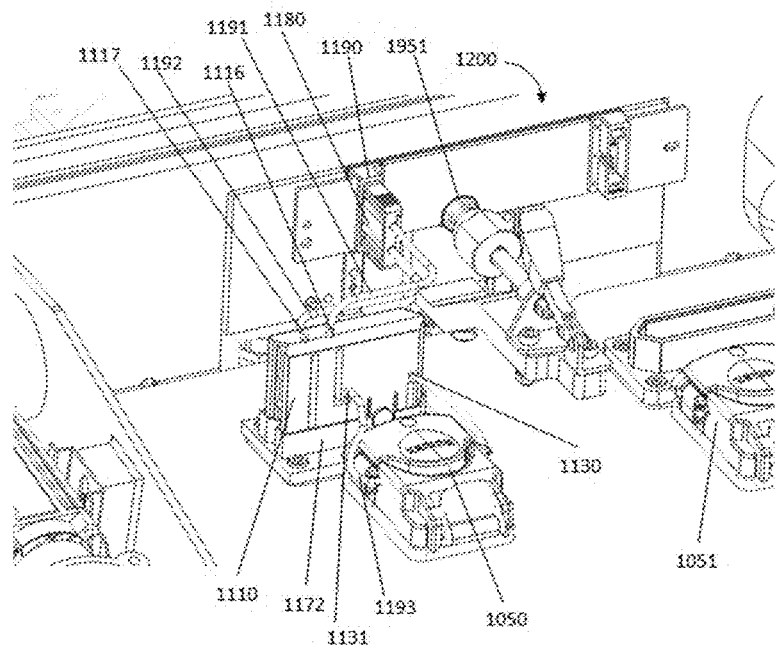
FIG. 12A shows a perspective view of the fluidic connection between a nucleic acid sequencing system and a flow cell.
Figure 12B:
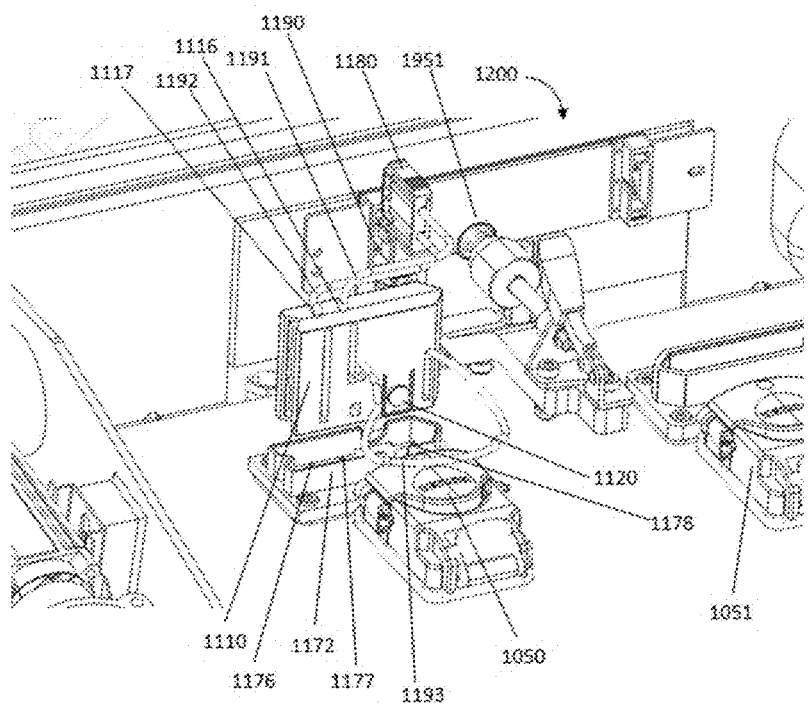
FIG. 12B shows the same perspective, but with the connectors disconnected.

In the view of FIG. 9, fluidic connections between routing manifold 1500 and flow cell 1200 have been removed and are instead shown in FIGS. 12A and 12B. The plurality of reservoirs 1400 is shown as the reservoirs are engaged by sipper array 1300. Also shown are drawers 1402 and 1403 which allow the user to replace liquids in the reservoirs. The reservoirs can be filled with reagents for a nucleic acid sequencing process. Exemplary reagents include, but are not limited to polymerases, nucleotides and other reagents set forth in Example 2, elsewhere herein, or in references cited herein, in the context of nucleic acid sequencing. Optionally, the nucleotides and/or polymerases can be exogenously labeled for example with luminophores, such as those set forth herein or in references cited herein.

Figure 10:
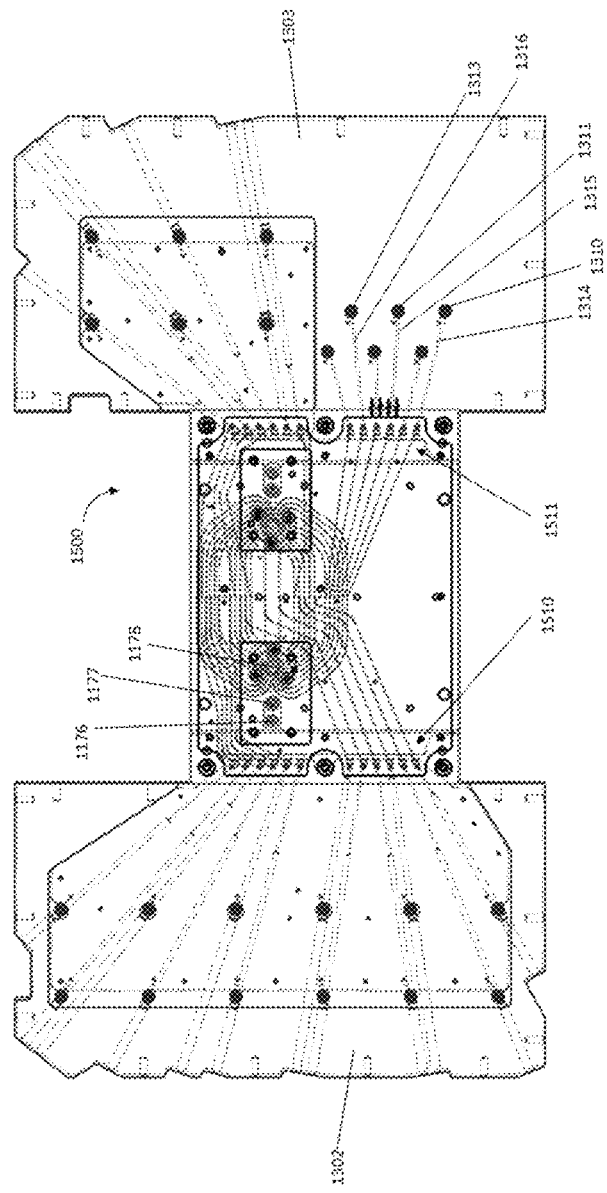
FIG. 10 shows a top view of a routing manifold fluidically connected to sipper arrays.
Figure 11:
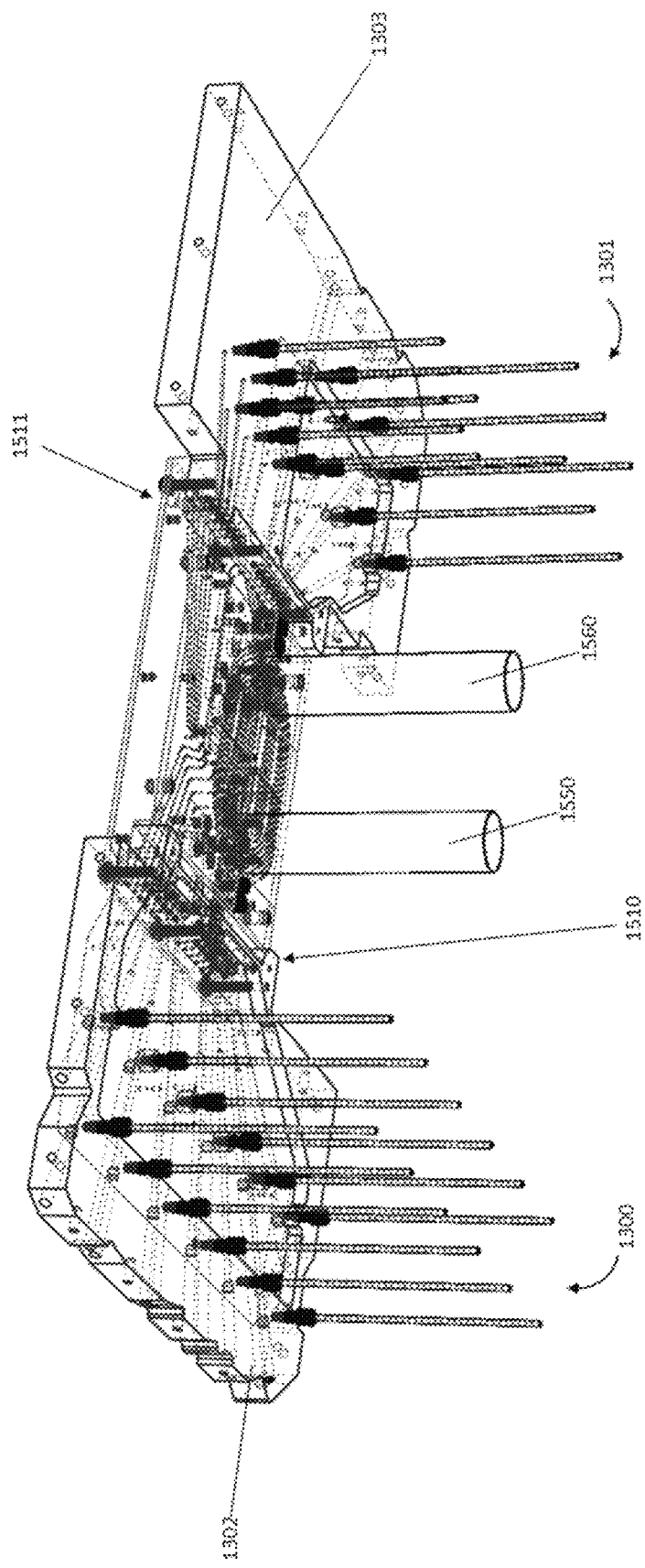
FIG. 11 shows a bottom view of routing manifold engaged with rotary valves.

FIG. 10 shows a top view of routing manifold 1500 fluidically connected to sipper manifold 1302 and sipper manifold 1303. Sippers attach to the sipper manifolds such that liquid drawn from a reservoir by the sipper is transferred through the sipper manifold to routing manifold 1500 by dedicated channels. For example, sipper manifold 1303 includes sipper attachment points 1310, 1311 and 1313 which are fluidically connected to fluid lines 1314 through 1316 within sipper manifold 1303. Fluid lines 1314 through 1316 connect to respective lines in routing manifold 1500 via connections 1500 to deliver the reagents to rotary valve 1560. FIG. 10 also shows connections 1510, on routing manifold 1500, which connect to respective connections on sipper manifold 1302 such that fluid drawn through the sippers can be directed to rotary valve 1550. Similarly, connections 1511, on routing manifold 1500, connect to respective connections on sipper manifold 1303 such that fluid drawn through the sippers can be directed to rotary valve 1560. Rotary valves 1550 and 1560 are visible in FIG. 11 which shows a bottom view of routing manifold 1500. FIG. 10 also shows egress port 1178 which connects the outflow of rotary valve 1550 to bubble generator 1100, fluidic ingress port 1176 which connects the egress of flow cell channel 1202 (FIG. 8) to waste tank 1800 (FIG. 8), and gas egress port 1177 which delivers gas from compressed air source 1350 (FIG. 8) to bubble generator 1100 (FIG. 8). Similar fluidic ports are present for rotary valve 1560.

Figure 13:
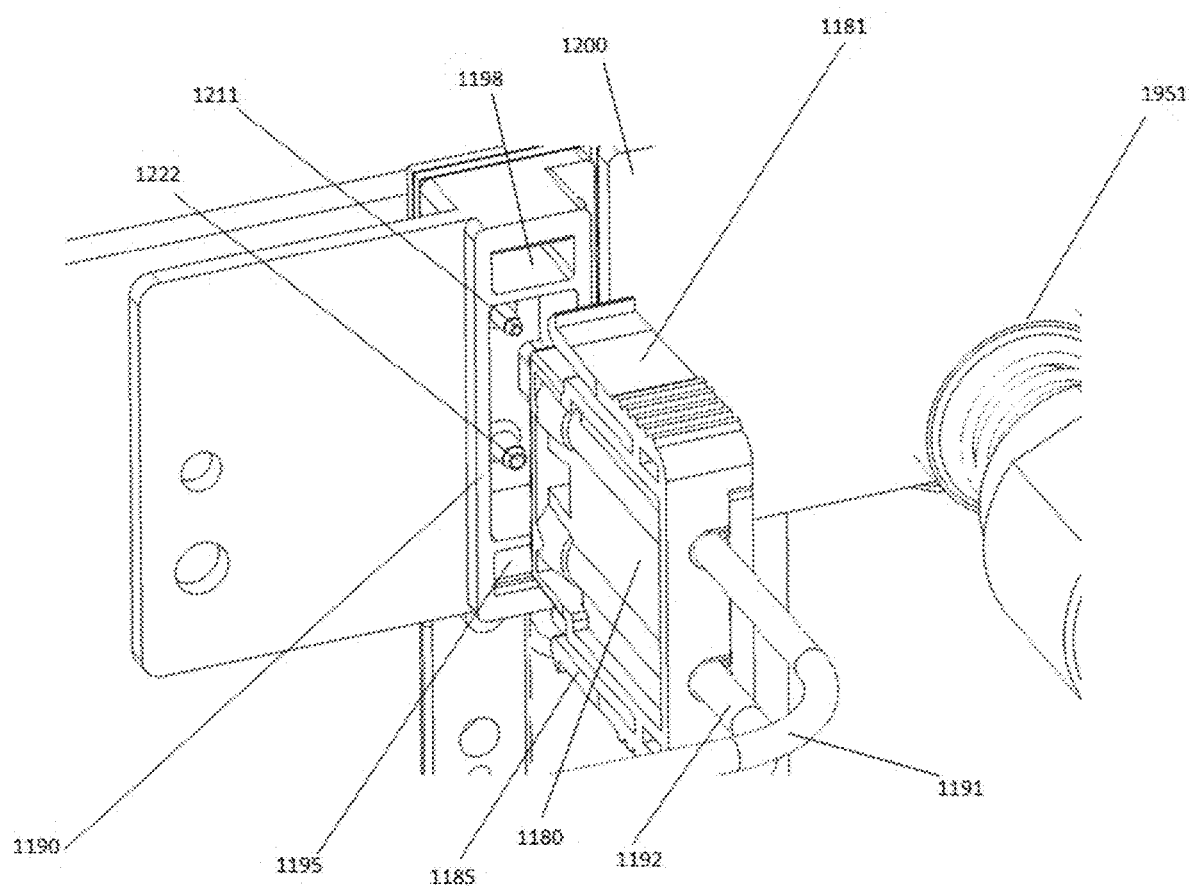
FIG. 13 shows the connection between a flow cell and the liquid delivery component of a nucleic acid sequencing system.

FIG. 12A shows a perspective view of the fluidic connection between nucleic acid sequencing system 1000 and flow cell 1200. FIG. 12B shows the same perspective, but with the connectors disconnected and slightly displaced. FIG. 13 shows the connection between flow cell 1200 and liquid delivery components of nucleic acid sequencing system 1000.

As shown in FIGS. 12A and 12B, the flow cell 1200 is fluidically connected to the instrument. Instrument connector 1110 engages with instrument connection port 1172. Instrument connection port 1172 contains gas egress port 1177 (FIG. 12B), fluid ingress 1176 (FIG. 12B) and liquid egress 1178 (FIG. 12B). Channels 1116 and 1117 of instrument connector 1110 are fluidically connected to flow cell connector 1180 by flexible tubes 1191 and 1192, respectively. Instrument connector 1110 can be engaged with instrument connection port 1172 by hand since the connector 1110 has compressible hook 1120 (FIG. 12B), which fits a complementary latch on instrument connection port 1176.

Also shown in FIG. 12A is peristalic pump 1050, which has a rotor that contacts flexible tube 1193 to apply positive pressure upstream of bubble generator 1100 (FIG. 8). Flexible tube 1193 passes from hole 1130 of instrument connector 1110, the over the rotor of peristaltic pump 1050, and then into hole 1131 of instrument connector 1110. Preload 1951 is also shown in FIG. 12A and FIG. 12B.

Regarding FIG. 13, the flow cell 1200 includes a flow cell connector 1180 engages with flow cell port 1190. Flow cell connector 1180 contains ingress 1211 for detection channel 1201 (FIG. 8) and egress 1222 for detection channel 1202 (FIG. 8). Instrument connector 1110 is configured to fluidically connect flexible tube 1191 to channel ingress 1211 and to connect flexible tube 1192 to channel egress 1222. Similarly, flow cell connector 1180 can be engaged with flow cell connection port 1190 by hand since connector 1180 has compressible hooks 1181 and 1185 that fit latches 1198 and 1195, respectively.

Figure 14A:
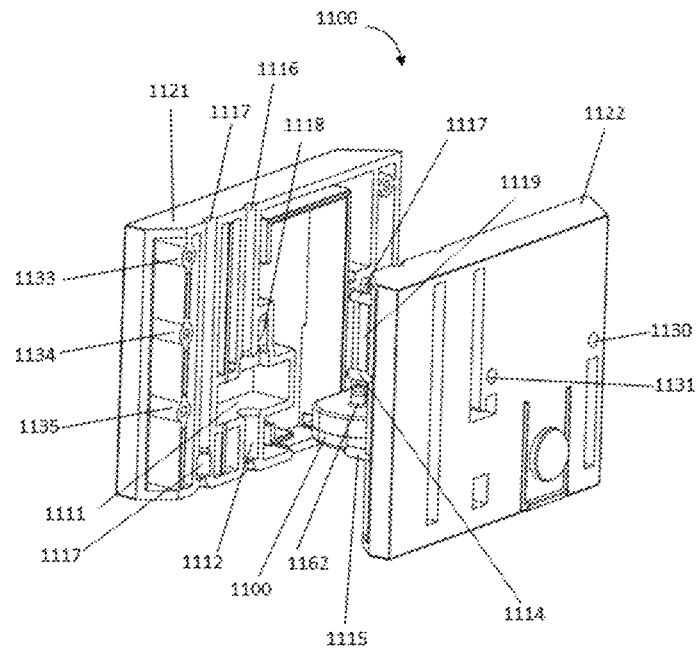
FIGS. 14A and 14B show exploded views of fluidic connectors that contain a bubble generator.
Figure 14B:
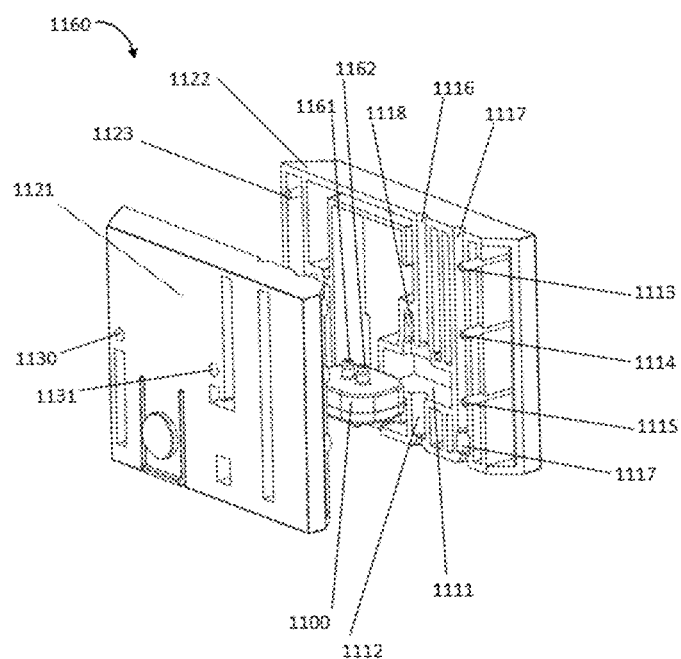

FIG. 14A shows an exploded view of left side instrument connector 1110, which connects fluidic components of system 1000 to the flow cell. FIG. 14B shows an exploded view of right side instrument connector 1160, which connects fluidic components of system 1000 to the flow cell. For ease of illustration, several elements of instrument connector 1160 are numbered the same as elements having similar function in instrument connector 1110. Instrument connector 1100 includes two plastic pieces 1121 and 1122, which can be assembled to contain bubble generator 1100. The two pieces can be snapped together, being held in place by compression fittings. The male components of the compression fittings 1113-1115 on piece 1122 snap into female fittings 1133-1135 on piece 1121. Bubble generator 1100 fits within pocket 1111 on pieces 1121 and a similar pocket on piece 1122.

When connector 1100 is assembled, liquid ingress port 1161 of bubble generator 1100 is in fluidic communication with flexible tube 1193 (FIGS. 12A and 12B). Flexible tube 1193 (FIGS. 12A and 12B) attaches to rotary valve 1550 (FIG. 11) via egress port 1178 (FIG. 10), passes through channel 1119 of connector 1110 then out hole 1130 (FIG. 12A) to loop around a rotor on peristaltic pump 1050 (FIG. 12A). Flexible tube 1193 (FIGS. 12A and 12B) then re-enters connector 1110 through hole 1131 (FIG. 12A) and passes through channel 1118 where flexible tube 1193 (FIGS. 12A and 12B) attaches to liquid ingress port 1161 on bubble generator 1100. Channel 1116 of connector 1110 connects to flexible tube 1191 (FIG. 13) such that foam exiting bubble generator 1100 at fluid port 1162 is directed to ingress 1211 (FIGS. 8 and 13) of detection channel 1201 (FIG. 8). Instrument connector 1110 also contains channel 1112 which connects the gas delivery component of nucleic acid sequencing system 1000 to bubble generator 1100. More specifically, gas from the gas delivery component is transferred from gas egress port 1177 (FIG. 10), through channel 1112 to gas inlet port 1163 (FIG. 15A) on bubble generator 1100.

Also included on instrument connector 1110 is channel 1117, which connects flexible tube 1192 (FIG. 13) to instrument fluidic ingress port 1176 (FIG. 10). As such, foam exiting detection channel 1202 (FIG. 8) via egress 1222 (FIG. 8) can travel through flexible tube 1192 (FIG. 13), then through channel 1117 (FIG. 14A), then through instrument fluidic ingress port 1176 (FIG. 10) to the routing manifold on its way to fluidic sensor 1600 or 1601 (FIG. 8), then downstream selector valve 1700 (FIG. 8) to waste tank 1800 (FIG. 8).

Figure 15A:
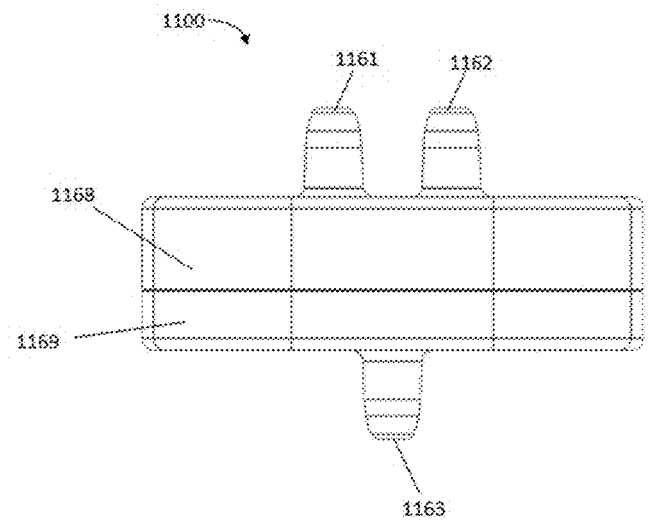
FIG. 15A shows a bubble generator.
Figure 15B:
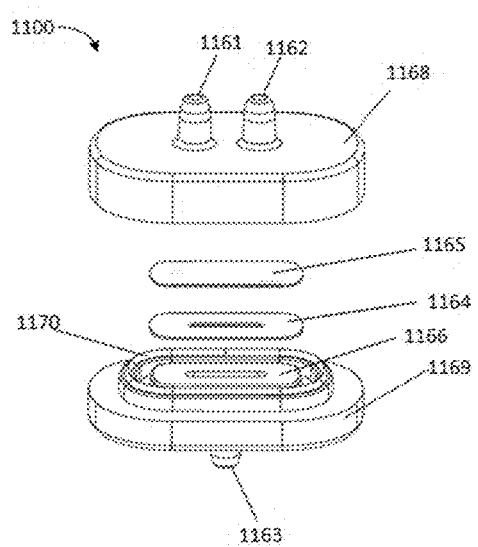
FIG. 15B shows an exploded view of the bubble generator.
Figure 15C:
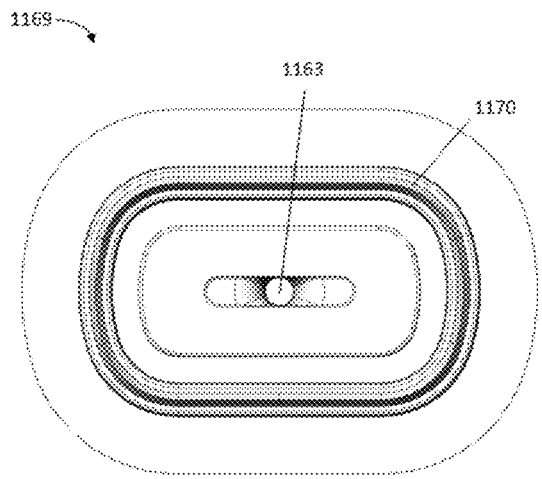
FIG. 15C shows the inside of one piece of the bubble generator and FIG. 15D shows the other piece of the bubble generator.
Figure 15D:
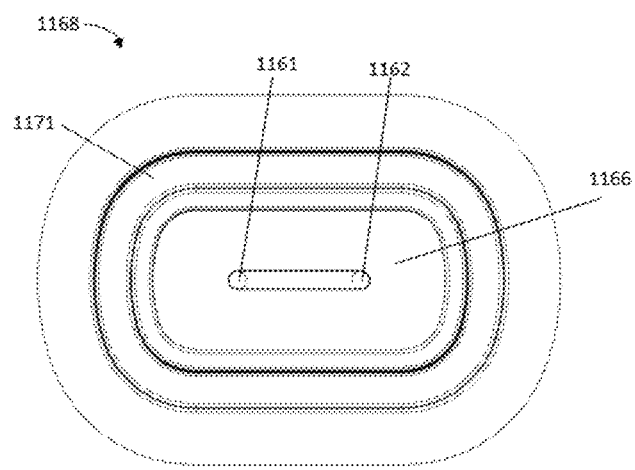

FIG. 15A shows bubble generator 1100, FIG. 15B shows an exploded view of bubble generator 1100, FIG. 15C shows the inside of piece 1169 of bubble generator 1100 and FIG. 15D shows piece 1168 of bubble generator 1100. The two outer pieces 1168 and 1169 (FIG. 15B) of bubble generator 1100 fit together via compression fitting between ridge 1170 (FIGS. 15B and 15C) and trough 1171 (FIG. 15D). Outer piece 1169 includes gas inlet port 1163 (FIGS. 15B and 15C). Outer piece 1168 includes liquid inlet port 1161 and foam outlet port 1162 (FIGS. 15A, 15B and 15D). The two pieces when assembled house gasket 1164 (FIG. 15B) and hydrophobic membrane 1165 (FIG. 15B) having an array of holes. The holes in the membrane have diameters between 1 μm and 80 μm and are not visible at the resolution of the figure. As shown in FIG. 15B, gasket 1164 has an elongated slit that, when sandwiched between face 1166 of upper piece 1168 and membrane 1165, forms a fluidic channel for liquid to flow from liquid inlet port 1161 and foam outlet port 1162. The liquid that passes through the gasket-formed channel will take up bubbles that pass into the channel from membrane 1165, thereby creating the foam.

Gas enters nucleic acid sequencing system 1000 from compressed air source 1350 such as a gas canister containing an inert gas or noble gas. Alternatively, compressed air source 1350 is an air compressor configured to deliver atmospheric air to bubble generator 1100. Compressed air source 1350 produces positive pressure on the gas that is delivered to the bubble generator. A useful air compressor is the Eagle EA 2000 having a single phase, 115 Volt, 44 dBA, 3.5 Amp motor; and having a single-stage, oil free, 50% duty cycle, pump that is CFM rated at 90 PSI and has a maximum PSI of 125. Gas from compressed air source 1350 is transferred to pneumatic controller 1300, which is configured to regulate and modify the delivery of the gas from the one or more sources into the liquid. Pneumatic controller 1300 is configured to vary the pressure of the gas, for example, in a range between 2 and 50 psi.

Example 3

Flow Cell Having Fluid Foam Inside

An exemplary flow cell includes a ternary complex immobilized inside a flow cell channel, wherein the ternary complex includes a polymerase, a primed template nucleic acid and a next correct nucleotide for the template; and a fluid foam that is in contact with the ternary complex in the flow cell channel, wherein the fluid foam includes a plurality of gas bubbles in a liquid, wherein the fluid foam includes a volume fraction of bubbles that is at least 25% of the total volume of the fluid foam in the flow cell channel, and wherein the average effective diameter of the gas bubbles is at most 95%, of the diameter of the flow cell channel.

Optionally, the polymerase in the flow cell is attached to an exogenous, luminescent label. Alternatively or additionally, the next correct nucleotide can be attached to an exogenous luminescent label.

Whether having labeled components or not, the ternary complex can be present at a site of an array of nucleic acids that is immobilized inside the flow cell channel. Optionally, the array includes at least $1 \times 10^3$ sites that have immobilized ternary complexes. Optionally, the average area for each of the sites in the array is less than 25 square microns. Each of the sites can include an ensemble of nucleic acids, each ensemble having nucleic acids having a common template sequence.

The ternary complex can be immobilized in the flow cell via attachment of the primed template nucleic acid to an inside surface of the flow cell channel. For example, the ternary complex can be immobilized via attachment of the primed template nucleic acid to a bead inside the flow cell channel. The primed template nucleic acid can be immobilized via linkage to the 5' end of the primer, via linkage to the 3' end of the template, or via linkage to the 5' end of the template.

The fluid foam can be flowing through the flow cell channel under positive pressure. However, the fluid foam can be static for at least some period of time during its use. The gas bubbles in the fluid foam can be substantially devoid of oxygen, for example, containing instead an inert gas or noble gas. Alternatively, a fluid foam can be composed of bubbles that contain atmospheric air or oxygen.

In addition to the immobilized components, the flow cell can contain free components that are solvated in the liquid phase of the fluid foam. For example, the fluid foam can contain free nucleotides. The free nucleotides can be present at any desired concentration, for example, at a concentration of at least 50 nM. The free nucleotides can have exogenous luminescent labels, blocking moieties (such as reversible terminator moieties), both types of moieties or neither type of moiety. Whether or not the fluid foam contains free nucleotides, the fluid foam can contain free polymerases. The polymerases can be present at any desired concentration, for example, a concentration of at least 5 units/ml.

Optionally, the cross-sectional area of the detection channel can be at most 100 mm$^2$. Alternatively or additionally, the cross-sectional area of the detection channel is at least 100 μm$^2$. The length and cross-sectional area of the detection channel can be adjusted to accommodate a desired volume of fluid foam. For example, the volume of the detection channel can be at most 1 ml. Alternatively or additionally, the volume of the detection channel is at least 1 μl. Other channel sizes can be used for example at a scale known in the art as microfluidic scale or nanofluidic scale.

The detection channel of the flow cell can optionally include an optically transparent window through which the ternary complex is visible. The window can be optically transparent to the wavelengths of light used for detection. For example, the window can be transparent to one or more of ultraviolet light, visible light or infrared light.

The primed template nucleic acid of the ternary complex can include a primer that is reversibly terminated or a primer having an extendable 3' end (i.e. the primer can have a 3' hydroxyl moiety). Optionally, the ternary complex can be a stabilized ternary complex. However, the ternary complex can, alternatively, be formed during a reaction that will incorporate the next correct nucleotide into the primer. As such, the ternary complex need not be stabilized nor inhibited from participating in polymerase catalyzed primer extension.

Optionally, the bubbles in the fluid foam can have an average effective diameter that is smaller than 500 μm. Alternatively or additionally, the bubbles in the fluid foam can have an average effective diameter that is larger than 500 nm. The fluid foam can contain surfactants, viscosity agents or other chemicals that alter the stability, size or other properties of bubbles in the foam.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:
1. A method for sequencing a nucleic acid, comprising
(a) providing a sequencing system comprising
  (i) a flow cell comprising a nucleic acid immobilized therein,
  (ii) a bubble generator component that delivers gas bubbles to a liquid at a predefined rate, wherein the bubble generator component comprises a filter membrane located at a junction through which the gas is delivered to the liquid;
(b) delivering a series of fluids to the inside of the flow cell to perform a cycle of a sequencing process, wherein at least one of the fluids is a fluid foam produced by the bubble generator component comprising gas bubbles in the liquid; and
(c) repeating step (b), thereby determining the sequence for the nucleic acid.
2. The method of claim 1, wherein the nucleic acid is immobilized on a surface inside the flow cell.
3. The method of claim 2, wherein the nucleic acid is present at a site in an array of nucleic acids immobilized on the surface.
4. The sequencing system of claim 3, wherein the sequencing process comprises optically resolving the site from other sites in the array.

5. The method of claim 1, wherein at least one of the fluids that is delivered to the flow cell is fluid foam containing a reversibly terminated nucleotide.

6. The method of claim 5, wherein at least one of the fluids that is delivered to the flow cell is fluid foam containing a deblocking reagent.

7. The method of claim 1, wherein at least one of the fluids that is delivered to the flow cell is fluid foam containing a fluorescently labeled nucleotide.

8. The method of claim 7, wherein the fluorescently labeled nucleotide comprises a reversible terminator moiety.

9. The method of claim 1, wherein at least one of the fluids that is delivered to the flow cell is fluid foam containing a polymerase.

10. The method of claim 9, wherein the polymerase forms a stabilized ternary complex with a fluorescently labeled nucleotide and the nucleic acid in fluid foam.

11. The method of claim 10, wherein the sequencing process comprises optical detection of the stabilized ternary complex.

12. The method of claim 9, wherein the polymerase covalently adds a fluorescently labeled nucleotide to the nucleic acid in fluid foam.

13. The method of claim 12, wherein the sequencing process comprises optical detection of the fluorescently labeled nucleotide added to the nucleic acid.

14. The method of claim 1, wherein the optical detection comprises irradiating the inside of the flow cell and collecting luminescence emission from the inside of the flow cell.

15. The method of claim 1, wherein the bubbles are substantially devoid of oxygen gas.

16. The method of claim 1, wherein the filter membrane comprises a hydrophobic material having a pattern of holes therein.

17. The method of claim 1, wherein at least one of the fluids that is delivered to the flow cell is substantially devoid of bubbles.

18. The method of claim 17, wherein the sequencing process comprises optical detection of the nucleic acid in the fluid that is devoid of bubbles.

19. The method of claim 1, wherein the delivering comprises delivering at least a portion of the fluid foam into the flow cell, out of the flow cell and back into the flow cell.

20. The method of claim 1, wherein the fluid foam comprises a volume fraction of bubbles that is at least 25% of the total volume of the fluid foam.

21. The method of claim 20, wherein the average diameter of the bubbles is at most 95%, of the diameter of the inside of the flow cell.

22. The method of claim 1, wherein the cross-sectional area of the inside of the flow cell is between 10 $\mu m^2$ and 100 $mm^2$.

23. The method of claim 1, wherein the volume of the inside of the flow cell is between 1 µl and 10 ml.

24. The method of claim 1, wherein the bubbles in the fluid foam have an average diameter that is between 500 nm and 500 µm.

* * * * *